(12) United States Patent
Beger et al.

(10) Patent No.: US 9,498,346 B2
(45) Date of Patent: Nov. 22, 2016

(54) SURGICAL IMPLANT FOR WIDENING A VERTEBRAL CANAL

(71) Applicant: Aesculap AG, Tuttlingen (DE)

(72) Inventors: Jens Beger, Tuttlingen (DE); Ralph Linke, Steisslingen (DE); Petr Suchomel, Liberec (CZ); Susanne Klingseis, Biberach (DE)

(73) Assignee: Aesculap AG, Tuttlingen (DE)

( * ) Notice: Subject to any disclaimer, the term of this patent is extended or adjusted under 35 U.S.C. 154(b) by 403 days.

(21) Appl. No.: 14/049,350

(22) Filed: Oct. 9, 2013

(65) Prior Publication Data

US 2014/0142699 A1    May 22, 2014

Related U.S. Application Data

(63) Continuation of application No. PCT/EP2012/055843, filed on Mar. 30, 2012.

(30) Foreign Application Priority Data

Apr. 12, 2011    (DE) ........................ 10 2011 001 996

(51) Int. Cl.
*A61F 2/44* (2006.01)
*A61B 17/70* (2006.01)
(Continued)

(52) U.S. Cl.
CPC ............... *A61F 2/44* (2013.01); *A61B 17/025* (2013.01); *A61B 17/0206* (2013.01); *A61B 17/1757* (2013.01); *A61B 17/7062* (2013.01); *A61B 17/7064* (2013.01); *A61B 17/7071* (2013.01); *A61F 2/4405* (2013.01); *A61B 17/683* (2013.01);

(Continued)

(58) Field of Classification Search
CPC ............ A61B 17/683; A61B 17/7062; A61B 17/7064; A61B 17/7071; A61F 2/44; A61F 2/4405

See application file for complete search history.

(56) References Cited

U.S. PATENT DOCUMENTS 5,980,572 A * 11/1999 Kim .................... A61B 17/7071
606/249
6,080,157 A   6/2000 Cathro et al.
(Continued)

FOREIGN PATENT DOCUMENTS

DE         602 12 648       6/2007
DE     20 2010 000 341      6/2010
(Continued)

OTHER PUBLICATIONS

F. Meyer et al., "Degenerative Cervical Spinal Stenosis", Deutsches Aerzteblatt International, vol. 105, Issue 20, pp. 366-372, 2008.
(Continued)

*Primary Examiner* — Larry E Waggle, Jr.
(74) *Attorney, Agent, or Firm* — Lipsitz & McAllister, LLC

(57) ABSTRACT

An implant is provided which allows for widening of the vertebral canal of vertebrae with less stress on the patient than in heretofore customary surgical procedures, wherein the vertebral arch of a vertebra is cut through, forming an incision gap, or is partially removed and the implant is inserted in the incision gap, wherein the incision gap is bounded by incision faces opposed to each other and the implant comprises an implant body having two contact faces which in the inserted state in the incision gap contact the incision faces of the vertebral arch.

23 Claims, 40 Drawing Sheets

(51) Int. Cl.
*A61B 17/02* (2006.01)
*A61B 17/17* (2006.01)
*A61B 17/68* (2006.01)

(52) U.S. Cl.
CPC .... *A61B 17/7028* (2013.01); *A61B 2017/0256* (2013.01); *A61B 2090/3966* (2016.02)

(56) References Cited

U.S. PATENT DOCUMENTS

| | | | |
|---|---|---|---|
| 6,572,617 | B1 | 6/2003 | Senegas |
| 6,635,087 | B2 | 10/2003 | Angelucci et al. |
| 6,652,593 | B2 | 11/2003 | Boyer, II et al. |
| 6,776,800 | B2 | 8/2004 | Boyer, II et al. |
| 6,855,169 | B2 | 2/2005 | Boyer, II et al. |
| 6,997,953 | B2 | 2/2006 | Chung et al. |
| 7,264,620 | B2 | 9/2007 | Taylor |
| 7,608,113 | B2 | 10/2009 | Boyer, II et al. |
| 7,753,963 | B2 | 7/2010 | Boyer, II et al. |
| 8,105,366 | B2 | 1/2012 | Null et al. |
| 8,133,280 | B2 * | 3/2012 | Voellmicke ........ A61B 17/7071 606/246 |
| 8,323,292 | B2 | 12/2012 | Dudasik et al. |
| 2002/0120335 | A1 | 8/2002 | Angelucci et al. |
| 2002/0120338 | A1 | 8/2002 | Boyer, II et al. |
| 2002/0120346 | A1 | 8/2002 | Boyer, II et al. |
| 2002/0120347 | A1 | 8/2002 | Boyer, II et al. |
| 2003/0045935 | A1 | 3/2003 | Angelucci et al. |
| 2003/0045936 | A1 | 3/2003 | Angelucci et al. |
| 2003/0050700 | A1 | 3/2003 | Kihara |
| 2003/0125738 | A1 | 7/2003 | Khanna |
| 2003/0125740 | A1 | 7/2003 | Khanna |
| 2004/0030388 | A1 | 2/2004 | Null et al. |
| 2004/0107003 | A1 | 6/2004 | Boyer, II et al. |
| 2004/0153155 | A1 | 8/2004 | Chung et al. |
| 2004/0210222 | A1 | 10/2004 | Angelucci et al. |
| 2004/0254428 | A1 | 12/2004 | Ritland |
| 2005/0107877 | A1 | 5/2005 | Blain |
| 2005/0131412 | A1 | 6/2005 | Olevsky et al. |
| 2005/0131548 | A1 | 6/2005 | Boyer, II et al. |
| 2005/0251138 | A1 | 11/2005 | Boris et al. |
| 2005/0273100 | A1 | 12/2005 | Taylor |
| 2006/0074431 | A1 | 4/2006 | Sutton et al. |
| 2008/0009865 | A1 | 1/2008 | Taylor |
| 2008/0215096 | A1 | 9/2008 | Nash et al. |
| 2009/0005882 | A1 | 1/2009 | Boyer, III et al. |
| 2009/0048675 | A1 | 2/2009 | Bhatnagar et al. |
| 2009/0177285 | A1 | 7/2009 | Frey et al. |
| 2009/0198240 | A1 | 8/2009 | Kaufman |
| 2009/0198278 | A1 | 8/2009 | Shibata et al. |
| 2009/0210012 | A1 | 8/2009 | Null et al. |
| 2009/0259107 | A1 | 10/2009 | Crenshaw et al. |
| 2010/0057127 | A1 | 3/2010 | McGuire et al. |
| 2010/0063590 | A1 | 3/2010 | Cannestra |
| 2010/0069960 | A1 | 3/2010 | Chaput |
| 2010/0114100 | A1 | 5/2010 | Mehdizade |
| 2010/0152745 | A1 | 6/2010 | Dudasik et al. |
| 2010/0152854 | A1 | 6/2010 | Slivka et al. |
| 2010/0161056 | A1 | 6/2010 | Voellmicke et al. |
| 2010/0185239 | A1 | 7/2010 | Patel et al. |
| 2010/0185240 | A1 | 7/2010 | Mangione et al. |
| 2010/0241165 | A1 | 9/2010 | Konieczynski et al. |
| 2010/0241230 | A1 | 9/2010 | Mazzuca et al. |
| 2011/0046680 | A1 | 2/2011 | Khanna |
| 2011/0106083 | A1 | 5/2011 | Voellmicke et al. |
| 2011/0106087 | A1 | 5/2011 | Gamache |
| 2011/0106168 | A1 | 5/2011 | Bucci et al. |
| 2011/0106169 | A1 | 5/2011 | Zalenski et al. |
| 2011/0166601 | A1 | 7/2011 | Cain |
| 2012/0078304 | A1 | 3/2012 | Jensen et al. |
| 2012/0165942 | A1 | 6/2012 | Khanna |
| 2014/0025113 | A1 * | 1/2014 | McCormack ........ A61F 2/4405 606/247 |

FOREIGN PATENT DOCUMENTS

| | | |
|---|---|---|
| EP | 2 196 160 | 6/2010 |
| EP | 2 091 446 | 10/2011 |
| JP | 2000139970 | 5/2000 |
| JP | 2001149392 | 6/2001 |
| JP | 2001170092 | 6/2001 |
| WO | WO 03/020143 | 3/2003 |
| WO | WO 2008/139260 | 11/2008 |
| WO | WO 2009/025884 | 2/2009 |
| WO | WO 2010/033567 | 3/2010 |
| WO | WO 2010/107546 | 9/2010 |
| WO | WO 2010/144636 | 12/2010 |
| WO | WO 2011/053523 | 5/2011 |

OTHER PUBLICATIONS

X. Wang, et al., "Prediction of Spinal Canal Expansion Following Cervical Laminoplasty: A Computer-Simulated Comparison Between Single and Double-Door Techniques", Spine, vol. 31, No. 24, pp. 2863-2870, 2006.

M. Wang, et al., "Minimally Invasive Cervical Expansile Laminoplasty: An Initial Cadaveric Study ", Neurosurgery, vol. 52, No. 2, pp. 370-373, Feb. 2003.

D. Benglis, et al., "Clinical Feasibility of Minimally Invasive Cervical Laminoplasty", Neurosurg Focus, vol. 25, pp. 1-4, Aug. 2008.

* cited by examiner

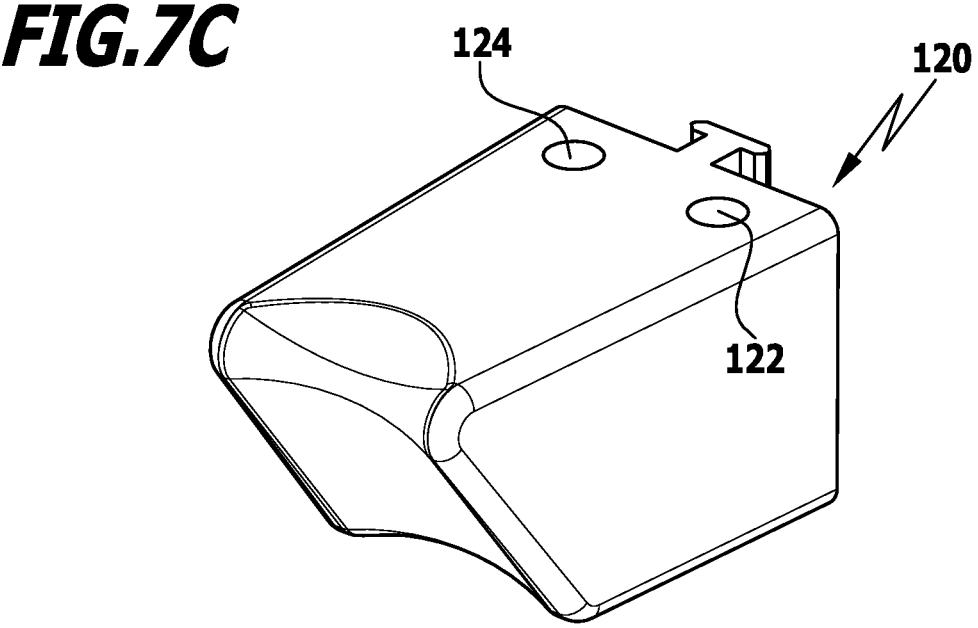
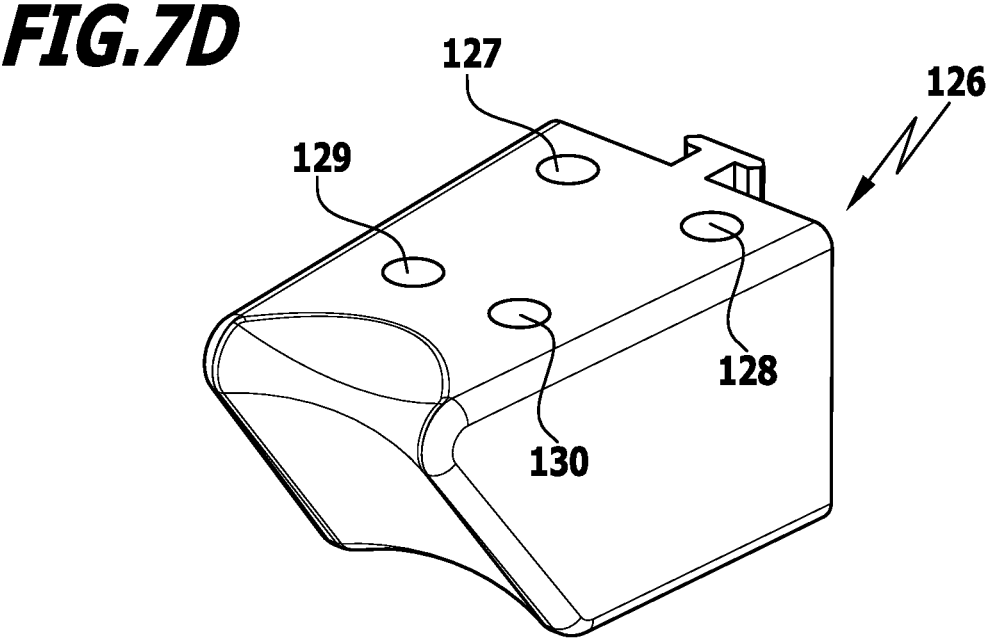

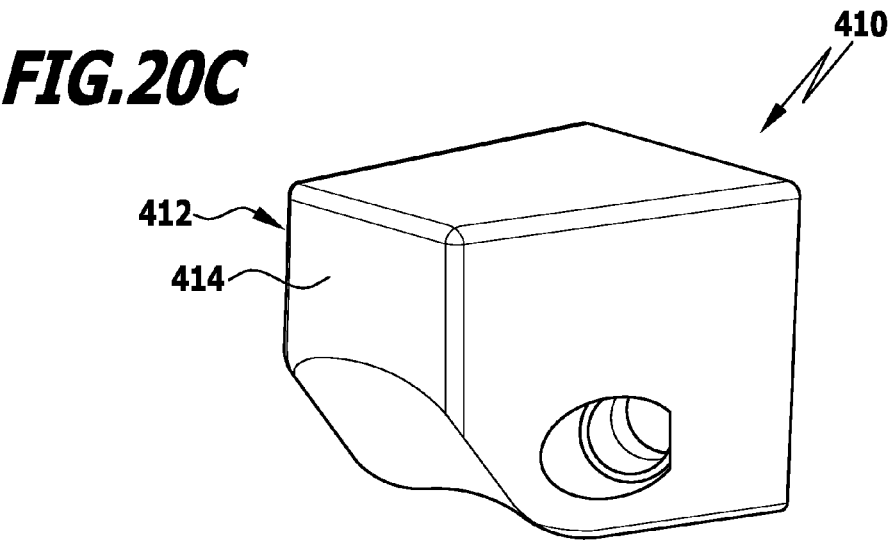
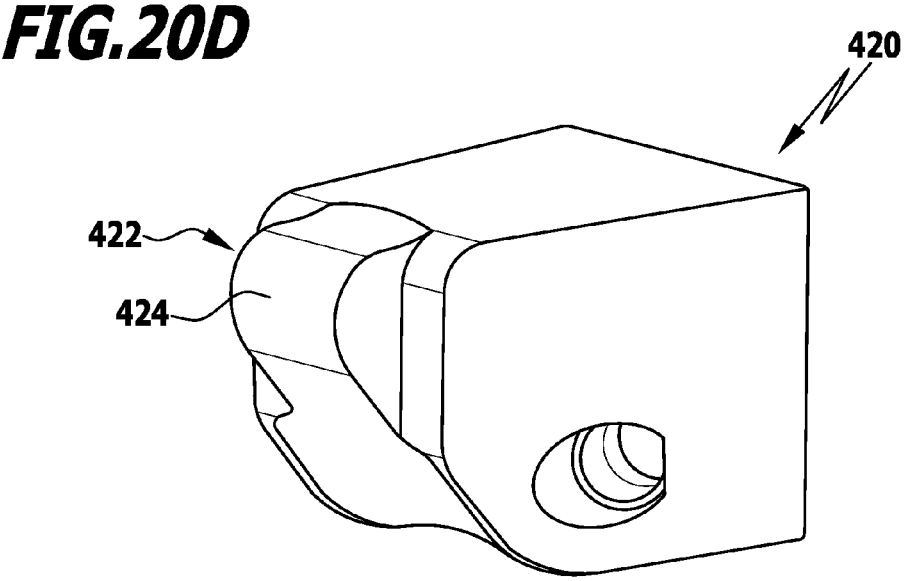

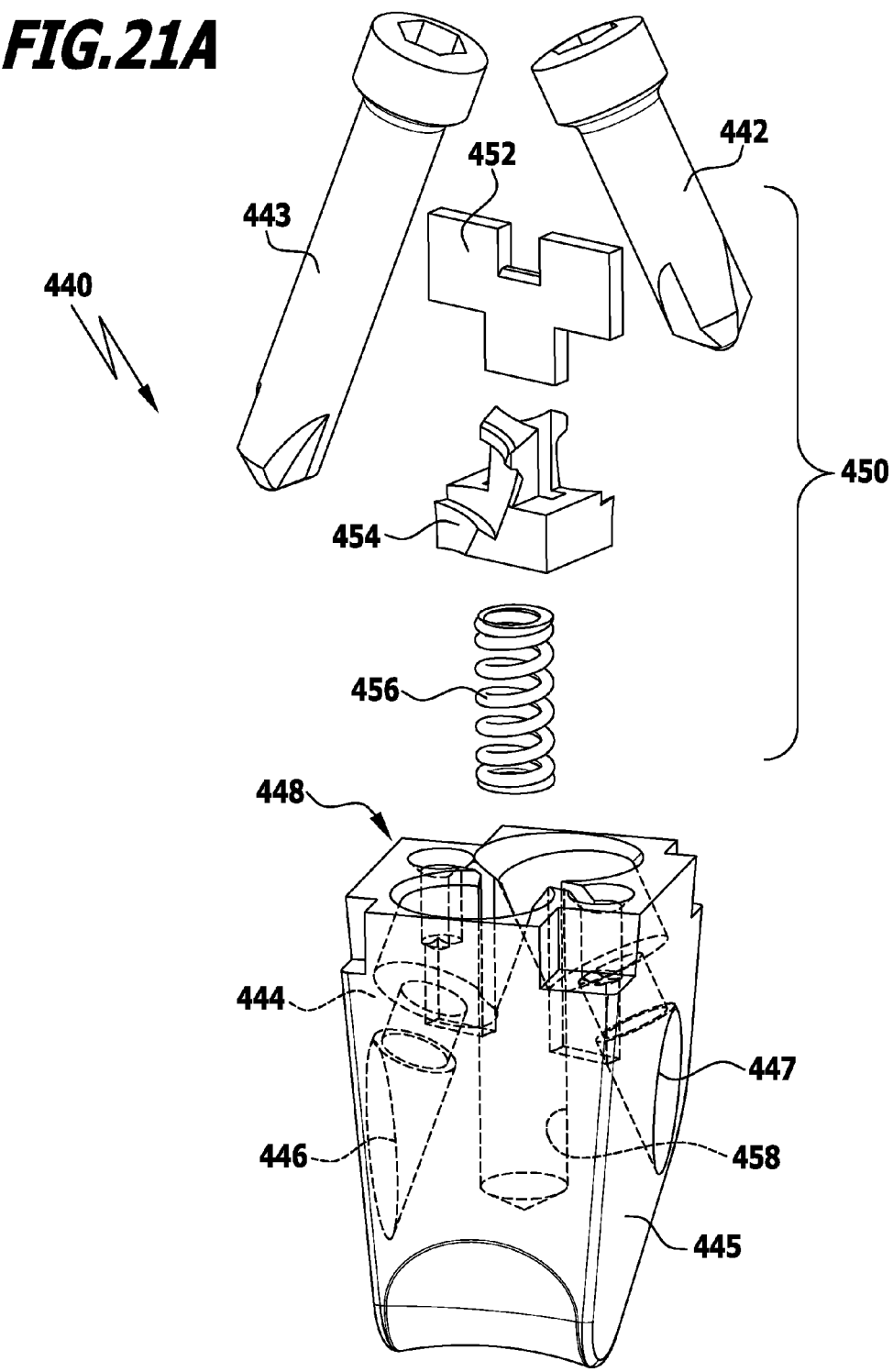

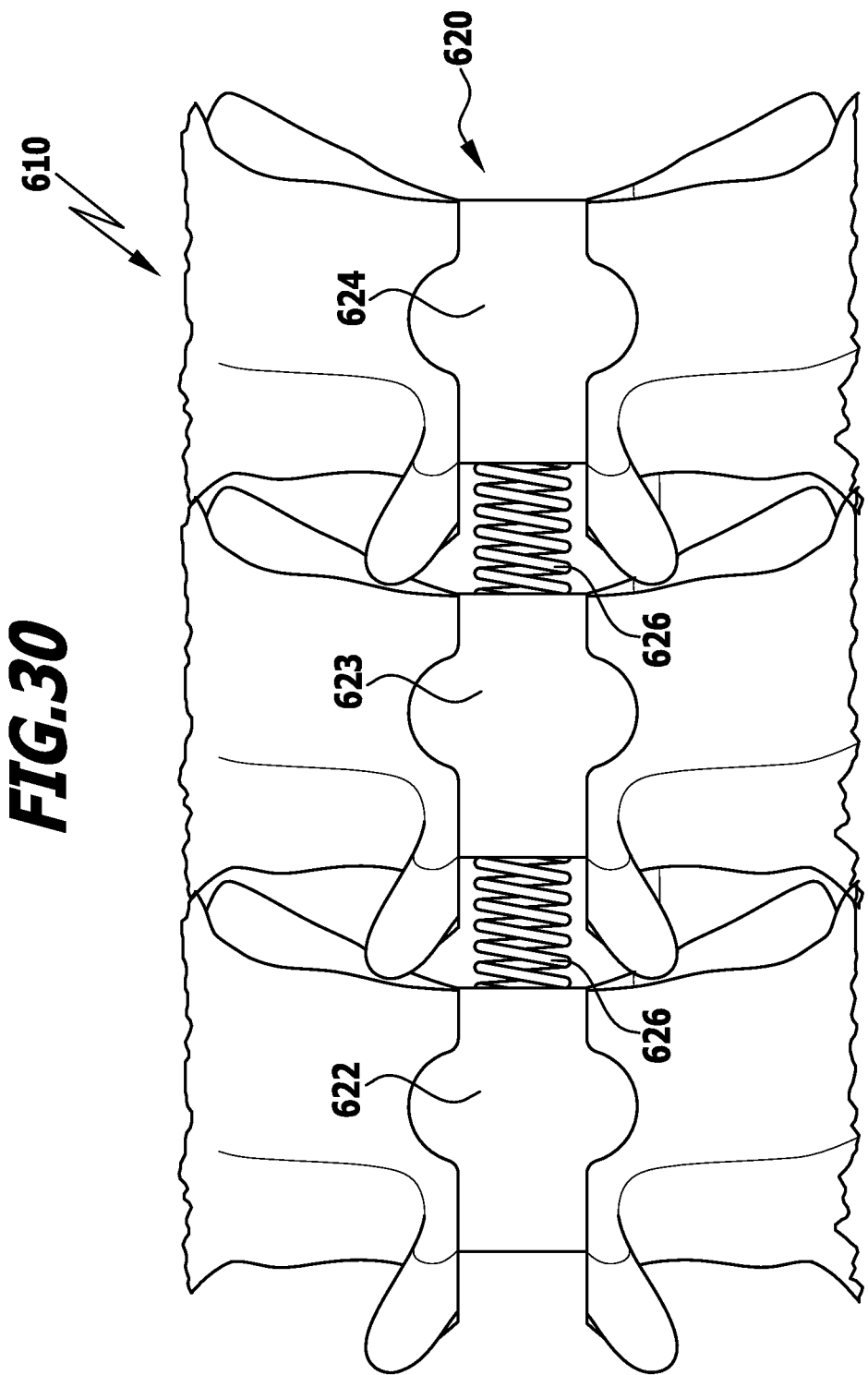

SURGICAL IMPLANT FOR WIDENING A VERTEBRAL CANAL

This application is a continuation of international application number PCT/EP2012/055843 filed on Mar. 30, 2012 and claims the benefit of German patent application number 10 2011 001 996.0 filed on Apr. 12, 2011, which are incorporated herein by reference in their entirety and for all purposes.

BACKGROUND OF THE INVENTION

The invention relates to a surgical implant for use in a method for widening a vertebral canal of a vertebra of the spine, in particular in laminoplasty and laminectomy methods.

The vertebral canals of the vertebrae of the spine form what is known as the spinal canal, in which the spinal cord, covered by the spinal meninges, is contained.

The spinal cord as part of the central nervous system may be impaired in its functions if pressure is exerted on the spinal cord, as occurs for example in spinal canal stenosis, a condition which can be attributable to a number of causes, such as the presence of spondylosis or ossification of the posterior longitudinal ligament.

This situation may be remedied by enlarging the vertebral canal of the vertebra or vertebrae of the spine that is or are affected so that the spinal cord has more space available to it and can therefore evade the pressure.

An overview of the therapy options commonly used to date can be found for example in F. Meyer et al., Deutsches Ärzteblatt, Volume 105, Issue 20, pages 366 to 372. Aside from the ventral methods, various dorsal methods are used, namely laminectomy with and without fusion and laminoplasty. Optionally, ventral methods may also be used in combination with dorsal methods.

Among the various dorsal methods, laminoplasty necessitates the least intervention in the bone substance.

Various surgical techniques for performing laminoplasty have been proposed heretofore, and of these the two most important are described and referred to in literature as the single door technique or the double door technique. An overview of these techniques and an assessment of the effects to be expected in terms of pressure relief and widening of the spinal canal may be found for example in the publication by Wang, Xiang-Yang et al. in SPINE, Vol. 31, No. 24, 2006, pages 2863 to 2870.

In what is known as the single door technique, also known as the open door technique, the lamina is cut through on one side of the vertebra, forming an incision gap, while a groove is created on the other side of the lamina, without the vertebral arch being cut through.

In the subsequent opening up of the vertebral canal, the region of the vertebral arch that has the groove acts as a kind of hinge and allows the vertebral arch to be opened, this being accompanied by fracture of the bone substance. The vertebral arch remains joined to the vertebral body by the periosteum and the collagenous fibres of the bone substance.

What is known as the double door technique involves cutting through or completely removing the spinous process of a vertebra and placing a groove in the lamina on each of the two sides of the spinous process; here again, the regions of the vertebral arch containing the grooves act as hinges. The vertebral canal is now opened up by swinging apart the two vertebral arch sections with the associated spinous process portions, if still existing, and as before the bone substance in the area of the hinges breaks. Here, too, the vertebral arch sections remain connected to the vertebral body by the periosteum and the collagenous fibres of the bone substance.

Using either technique, the vertebral canal of the vertebrae is fixed in the opened up state by way of implants. Aside from autologous bone graft, a hydroxyapatite spacer or the like is used as an implant material.

Despite the reduced degree of intervention in the bone substance as compared with other dorsal methods, a significantly increased rate of subsequent neck pain is still regarded as a disadvantage of laminoplasty, as is a restriction in motion of the cervical spine which is often observed.

It is an object of the invention to propose an implant which enables widening of the vertebral canal of vertebrae with less stress on the patient.

SUMMARY OF THE INVENTION

This object is accomplished by a surgical implant having the features of claim 1.

The contact faces of the implant constructed in accordance with the invention may be oriented substantially parallel to each other, in particular where the implant is to be used in a laminectomy setting.

In many instances, in particular where the implant constructed in accordance with the invention is used in a laminoplasty setting, the implant constructed in accordance with the invention has contact faces that are inclined relative to each other in the shape of a wedge, wherein the distance between the contact faces is larger at a dorsal end region of the implant body than at a ventral end region thereof which in the implanted state of the implant is positioned adjacent to the spinal canal.

Designing the implant in accordance with the invention with contact faces that are inclined relative to each other in the shape of a wedge allows the implant to be in contact over a large area thereof with the incision faces of the bone substance of the vertebral arch. This promotes precise insertion, secure holding and permanent positioning of the implant in the incision gap.

The implant constructed in accordance with the invention is particularly suited for a laminoplasty method in which the vertebral arch of a vertebra is cut through, forming an incision gap, preferably in the area of the spinous process, and the incision gap is widened to a predetermined gap width as the bone substance of the resulting vertebral arch sections is elastically/plastically deformed.

An essential difference of this method compared with the previously discussed single and double door techniques of laminoplasty is on the one hand that only a single through-cut is made on the vertebral arch and the need for stripping muscles off the spine is eliminated to a large extent or is essentially even avoided entirely. Furthermore, fracture of the bone substance of the lamina does not occur, since the widening of the vertebral arch is achieved by way of elastic/plastic deformation of same.

Due to the inherent viscoelastic properties of the bone substance, the elastic/plastic deformation occurs additionally with this method, but without this leading to fractures of the bone substance. It is preferred for the widening not to be forced abruptly but to be performed gradually so that the viscoelastic properties of the bone substance can become effective. This can be done continuously or in small increments of for example about 0.5 mm to about 3 mm each. Typically, a gap widening of about 15 mm within about 10 sec to about 5 min, in particular within about 30 sec to about 3 min, more preferably within about 1 min to about 2 min, can be achieved in this way for the C6 vertebra.

This counteracts the problem of the laminoplasty techniques heretofore in use, which first necessitate extensive intervention in the muscles extending parallel to the spine, which also means considerable stress for the patient in the postoperative phase.

In particular, this method works with considerably less surgical intervention than does the prior art and with no lateral detachment of the muscles from the spine.

In particular when the through-cut is made in the area of the spinous process, then the location on the vertebra is very easy to access and the muscles parallel to the spine can remain substantially untouched.

A large variety of tools may be used to create the incision gap. For example, the incision gap can be made using an ultrasonic osteotome, with incision gaps of about 1 mm or less resulting.

Specially designed distraction instruments, in particular distraction forceps, are preferably used for the elastic/plastic widening of the incision gap, and it is preferred for these to be equipped with guide elements for safe placement of an implant, more preferably to comprise a measuring unit for indicating the incision gap widening achieved.

In view of the further steps, such as deploying the implant constructed in accordance with the invention, it is preferred for a distraction instrument to be used the tips or end regions of which are angled or have outwardly protruding projections. The angled tips or the projections can be slid under the lamina, i.e., they contact the spinal canal side of the lamina, thus ensuring secure seating during widening of the incision gap.

The forces required for widening the incision gap are typically about 70 N to about 200 N, in particular about 80 N to about 150 N, for widening the gap by about 5 mm to about 12 mm, determined in each case at the spinal canal side end of the incision gap.

The incision faces of the incision gap are fixed in the widened position via implants constructed in accordance with the invention.

The material used for fabrication of the implant constructed in accordance with the invention is preferably a body-compatible plastics material, in particular PEEK, or titanium or a titanium alloy. Aside from these, autologous bone graft is also suitable.

Implants made from a plastics material, in particular PEEK, are preferably provided with an osseointegration-enhancing coating on the surfaces thereof contacting the bone material. Preferably, said coating is produced as a microporous pure titanium layer using the VPS process (Plasmapore technique) or as a hydroxyapatite layer.

The plastics implants are preferred over titanium implants because they are compatible with MRI procedures. This is of particular importance for the postoperative phase. MRI compatibility is also present in the above-mentioned plastics implants having an osseointegration-promoting coating.

Implants made of titanium preferably have a porous structure or a lattice structure.

The implant constructed in accordance with the invention has the shape of a wedge so that as full surface contact as possible of the surfaces of the wedge-shaped body with the incision faces of the widened incision gap is achieved, with said incision faces, while after formation of the incision gap being first arranged parallel relative to each other, being inclined relative to each other in the shape of a wedge as a result of the elastic widening of the incision gap.

The contact faces, arranged in the shape of a wedge, of the implant constructed in accordance with the invention preferably define therebetween an angle of about 5° to about 45°, in particular 7° to 30°.

The implants constructed in accordance with the invention can also be used in conventional laminoplasty methods as well as in laminectomy.

Advantageously, guide elements are arranged at the contact faces of the implants constructed in accordance with the invention. Said guide elements are preferably formed as projections or recesses.

The projections or recesses of the preferred implants constructed in accordance with the invention may, in particular where corresponding recesses are provided in the incision faces of the incision gap, serve to guide the implant while it is inserted in the incision gap and on the other hand stabilize the implanted implants in their position.

Preferably, the recesses are, both on the implant side and the incision gap side, formed as grooves which are preferably of about semi-cylindrical form and are preferably oriented parallel to the dorsal-ventral longitudinal axis of the implant body or the incision gap.

A further aspect lies in guiding the implant bodies during their insertion into the incision gap, with the projections of the contact faces of the implant bodies slidingly engaging the grooves of the incision faces.

The grooves in the incision faces may also act as a positioning aid for the distraction instruments. If the implant bodies are to be inserted into the incision gap immediately after the vertebral arch sections have been sufficiently distracted, then the distraction instrument, partly received by the grooves, can remain in place in the incision gap and hold same in its widened position while implants, preferably provided with corresponding grooves at their contact faces, are inserted into the incision gap, guided by the distraction instrument.

Furthermore, the guide elements in the form of projections, which are preferably provided at the contact faces of the implant bodies, can be used to form in the inserted state a stop at the bone substance so that the implant constructed in accordance with the invention can be inserted into the incision gap only to a predetermined depth. In particular, this ensures that the implant cannot intrude on the spinal canal space with its ventral end region. This arrangement also secures the correct position of the implant for the future.

To this end, the projections need not necessarily have a larger extension in the longitudinal direction of the implant body. However, a longer extension is desirable in particular in those instances where it is desired for the guiding function of the projections in combination with the recesses on the incision face side of the incision gaps to become effective.

In a more preferred embodiment of the implants constructed in accordance with the invention, the projections or recesses in the dorsal end region are arranged off-centre in the sagittal direction. This makes it possible for the projections or recesses to be arranged at a sagittal position of the incision gap that is at least partially outside the area of the spinous processes. In such a case, easier access to the further functional parts which are often arranged in lieu of projections on the implant body side and which will be discussed in the following is given.

The implant body may be provided with an alternative or further guide element at its ventral end region, said guide element preferably being configured such that it can be introduced between the arms of a distraction instrument and guided along said arms in a direction towards the incision gap of the vertebra and thereby inserted into the incision gap.

Preferably, the height of the implant is adapted to the depth of the incision gap, thus resulting in a maximum surface area for contact of the implant with the incision faces and hence low surface pressure on the bone substance side. This is also of importance in consideration of the fact that the implant remains permanently in a patient's body.

In accordance with the invention, a variety of ways exist by which the implants can be fixed to the bone material by their implant body inserted in the incision gap.

The previously mentioned formation of recesses in the incision faces and of projections in the contact faces of the implant bodies constructed in accordance with the invention can be used to create a form-locking engagement between the incision gap or the bone substance of the vertebra and the implant.

Moreover, the forces acting on the implant body due to the elastic/plastic widening of the vertebral arch lead to a certain initial force-locking engagement. This will, however, diminish over time due to the viscoelastic properties of the bone substance.

Therefore, provision may preferably be made for the implant body to be anchored to the bone substance by use of additional fasteners.

For example, the implant body constructed in accordance with the invention may have one or more bores through which the implant body can be fixated by way of pins or screws which engage the bone substance.

A further alternative consists of fixating the implant bodies to the vertebral arch using suture material or wire. Likewise, metal or plastic bridges which engage over the implant body can be fixed on either side of the incision gap to the bone substance in order to hold and secure the implant body in place in the incision gap.

Thus, preferred implants comprise an implant body having one or more transverse bores which are oriented transversely to the longitudinal direction of the wedge-shaped implant body. These transverse bores form channels allowing suture material to be guided therethrough, and said suture material can, on the vertebra side, be connected for example to the spinous processes. Such transverse bores are preferably arranged parallel or perpendicularly to the contact faces.

Where implants of larger depth are used, a plurality of transverse bores distributed along the longitudinal direction of the implant body are advantageous because this then allows the ventral-side end region of the implant body to be connected to the vertebral arch, while the dorsal end region can for example hold, separately fixed thereto, sections of the spinous process that have broken off.

Alternatively, the transverse bores can also be used to receive on the implant side fixation elements, such as screws, dowels etc., which penetrate from the exterior, i.e., through the bone substance. This then does not require through-bores; blind bores will be adequate. Where the implant body is made of a PEEK material, it is preferred for the fixation elements, in particular the screws or dowels, to be likewise made of PEEK material.

In a preferred embodiment of the implants constructed in accordance with the invention, the implant body has bores that are formed as through-bores and which, starting from the dorsal end region, are oriented at an acute angle with respect to the contact faces of the wedge-shaped implant body and preferably extend through the contact faces. Said bores form guides for fastening elements, such as spikes, dowels and screws or splints, which can, guided in said bores on the implant side, be inserted, screwed or driven into the bone material adjacent thereto in the implanted state.

The angle with respect to the sagittal plane of symmetry in which the axes of the through-bores are oriented is preferably in the range of about 10° to 60°, in particular about 15° to about 45°.

The angles are selected from the perspective of allowing as long a bore section or threaded section as possible to be achieved in the bone substance of the vertebral arch, while at the same time preventing the fastening elements inserted in the bore or thread from intruding into the spinal canal. The longer the bore or threaded section can be made in the bone substance, the more securely the implant can be anchored.

Where the implant is in the shape of a wedge which has the contact faces inclined with respect to each other at an angle of for example 10°, it has in many cases proven advantageous to use angles of about 20° to about 30° for the axes of the through-bores.

Other preferred implants constructed in accordance with the invention comprise a locking element which is preferably integrated in the body and which can be activated after positioning the implant body in the incision gap. The locking element is preferably fabricated from the same type of material as the implant body that is fitted with same.

By way of example, bone screws whose flanks are arranged in a rotational position within the implant body and which, upon rotation through about 90°, protrude beyond the contact faces of the implant body and cut their way into the surrounding bone substance may be used as locking elements.

A further alternative for fixing the implant body in the incision gap consists of establishing a form-locking connection or a substance-to-substance-bond of the implant body with the surrounding bone substance. Materials suitable for the form-locking connection or the substance-to-substance bond include plastifiable or curable materials or what are known as hot-melt adhesives which can be activated by ultrasound, heat, HF or also UV light.

The projections on the implant side are then preferably of semi-cylindrical configuration to conform to the shapes of the grooves so that contact over as large an area as possible is also ensured in the area of the projections and recesses of the bone material and the implant.

Preferably, the implants constructed in accordance with the invention have in their implant body a rotational bearing for the locking element.

Alternatively, provision may be made for a blind bore which opens dorsally, extends substantially parallel to the longitudinal axis of the implant body and can receive a locking element provided with an external thread and having an outer perimeter that is larger than the distance between the contact faces at the dorsal end region of the implant body. When the locking element is screwed into the blind bore, which then preferably contains an internal thread formed therein, the external thread of the locking element cuts its way into the surrounding bone substance of the vertebral arch, thus securing the implant constructed in accordance with the invention in a correct seating position in the incision gap of the vertebral arch.

In a further alternative embodiment of the present invention, provision may be made for the implant body of the implant constructed in accordance with the invention to have provided therein a fixation device comprising one or more spike-like fixation elements. For these fixation elements, which in the non-implanted state are arranged in an inoperative position within the implant body, an actuating device is provided which can then transition the fixation elements to an operative position, wherein the tips of the fixation elements then emerge from the inoperative position within the contour of the implant body to an operative position, passing through openings preferably provided in the contact faces of the implant body, and penetrate the surrounding bone substance.

Alternatively, provision may be made for the implant body to be provided with articulately arranged snap-on elements which after insertion of the implant in the incision gap are, via a kind of sliding guide, moved in a direction substantially transverse to the contact faces towards the outside and can thus be pressed into the surrounding bone substance. To this end, the fixation elements preferably have undercut areas so that secure seating of the implant in the incision gap results by form-locking engagement. This embodiment implements a kind of dowel principle.

In a further embodiment of the implant constructed in accordance with the invention, provision may be made for the implant body to have an essentially centrally arranged through-opening which extends from the dorsal end region to the ventral end region of the implant body. The terms dorsal and ventral are used to mean proximal and distal respectively, as viewed by the surgeon.

Said through-opening may for example receive an actuating element of an anchoring device, said anchoring device comprising, on the ventral end region side of the implant body, a sheet element which has in at least one direction of its extension a width that is larger than the distance between the contact faces of the implant body at the ventral end region. The holding device preferably extends through the central through-opening to the dorsal end region, where it is capable of being fixed in its use position.

The sheet element is preferably elastically deformable and is, in a first position, held in an elastically deformed state at or in the implant body so that the extension of the deformed sheet element in a direction of the distance between the contact faces is smaller than the distance between the contact faces at the ventral end region of the implant body.

In the inserted state of the implant constructed in accordance with the invention, the sheet element is then moved out of said first position and pulled against the ventral end region of the implant body by way of a holding device, preferably by way of the holding device held for displacement in the through-bore, and is fixated in this position. In this process, the elastically deformed sheet element will assume an extension that is larger than what corresponds to the distance between the contact faces of the implant body at the ventral end region so that the sheet element contacts not only the ventral end region of the implant body but also the surrounding bone substance of the vertebral arch. In this way, the wedge-shaped implant of the present invention can be securely held in the incision gap of the vertebral arch.

Preferably, the snap-on elements, the locking elements, the fixation devices and associated fixation elements and the holding devices used with the previously described implants constructed in accordance with the invention are made from a material of the same type as that used for the implant body that is fitted with same, in particular a PEEK material.

In a further preferred embodiment of the invention, the implant body is configured in the shape of a cone or truncated cone. For this implant constructed in accordance with the invention, the incision gap of the vertebral arch is preferably prepared by forming therein a bore engaging the incision faces so that a guiding action results for the tip of the conical implant during insertion of same.

More preferably, the conical implant body has on its surface a circumferentially extending external thread which, when the implant is inserted or screwed into the vertebral arch, cuts its way into the adjacent bone substance.

With this type of implant constructed in accordance with the invention, the incision gap can be widened by the screwing-in of the implant.

The conicity of the implant body preferably corresponds to a cone angle of about 5° to 45°, in particular about 7° to about 30°.

In preferred implants of the present invention, the ventral end region of the implant body is of convex configuration so that additional room is created on the spinal canal side even though the contact faces of the implant body are supported on substantially the entire incision face of the incision gap.

Preferably, a grip element is provided at the dorsal end region of the implant constructed in accordance with the invention, which provides a simple way of grasping the implant with a tool and inserting it in the incision gap.

Instead of a grip element integrally formed thereon, the implant may also have bores which open at the dorsal side and extend substantially parallel to the longitudinal direction of the implant body. Said bores can have holding elements inserted or screwed therein, thus providing secure and optionally guided insertion of the implant into the incision gap by way of instruments.

Preferred implant bodies have at their ventral end region a distance between the contact faces arranged in the shape of a wedge that is about 5 to about 15 mm. This fixes, via the implant constructed in accordance with the invention, a corresponding distance between the incision faces of the incision gap; this distance may also be somewhat smaller than the above-mentioned distance for the case that the ventral end region of the implant does not quite extend down to the spinal canal.

These and further advantages of the invention are described in more detail below with reference to the drawings.

BRIEF DESCRIPTION OF THE DRAWINGS

FIGS. 7A to 7F are perspective and side views of a third embodiment of the first basic form of the implant constructed in accordance with the invention and various further variants thereof;

FIGS. 20A to 20D are perspective views of further variants of the third embodiment of the first basic form of the implant constructed in accordance with the invention;

FIGS. 21A to 21C are various details of a further variant of the third embodiment of the first basic form of the implant constructed in accordance with the invention;

FIG. 30 shows a second embodiment of a multiple implant constructed in accordance with the invention and based on the first basic form, in the implanted state;

DETAILED DESCRIPTION OF THE INVENTION

Figure 1A:
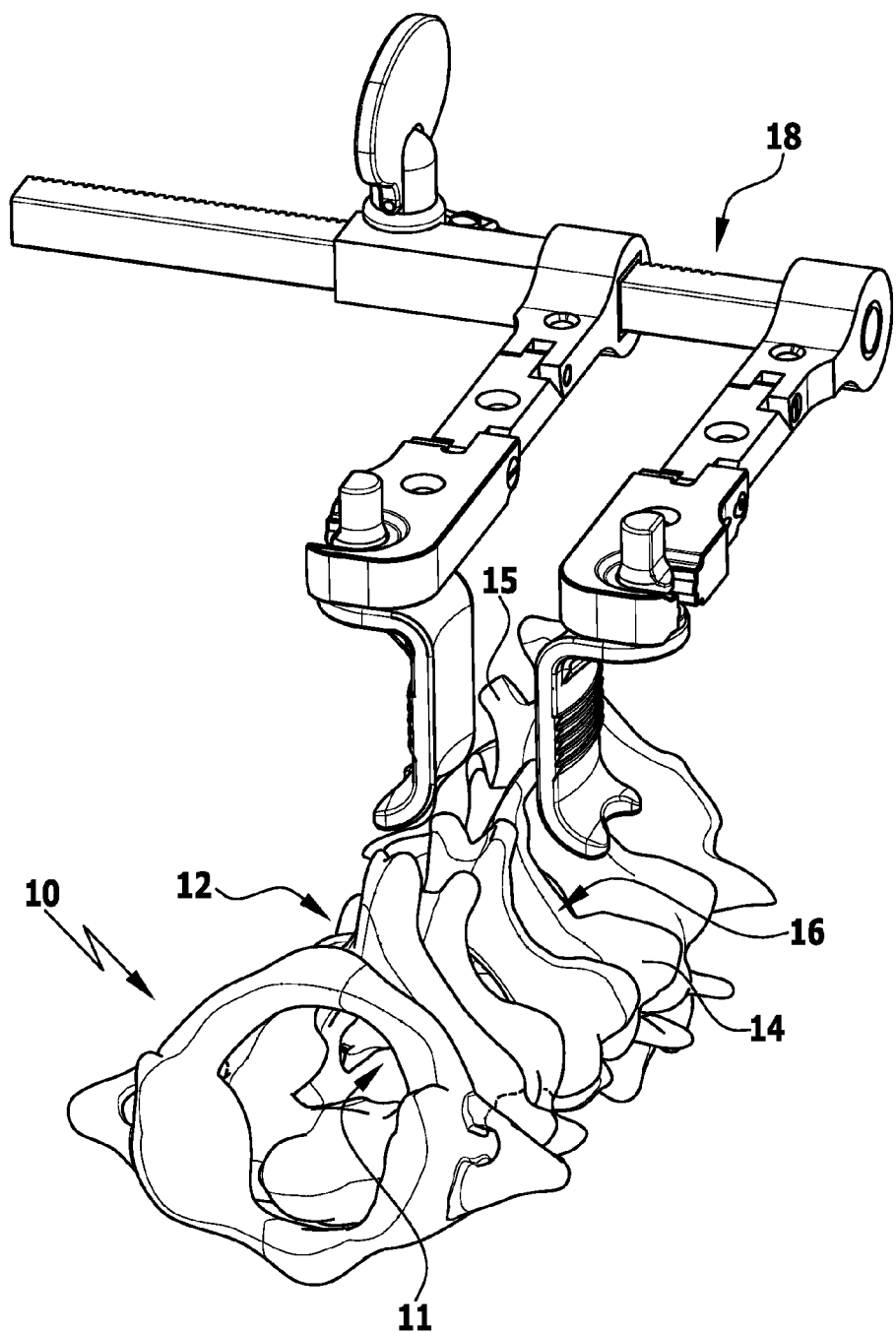
FIGS. 1A and 1B are a perspective view and a top view respectively of a part of the cervical spine, illustrating a cervical vertebra provided with an incision gap.

FIG. 1A is a schematic representation of the C1 to C7 section of a cervical spine 10 with a spinal canal 11 and a retractor 18, the latter being positioned over a vertebral arch 12 of a vertebra 14 and holding back the surrounding tissue (omitted from FIG. 1 in the interest of clarity) so that dorsal access to the area of the vertebra 14 is maintained.

In accordance with the invention, the vertebra 14 and its vertebral arch 12 can be accessed without stripping off muscle tissue, thereby giving access to its spinous process 15, whereas access to the lamina 16 requires muscle tissue to be stripped.

In the state as viewed in FIG. 1A, an instrument (not shown) can be used to create in the area of the lamina 16 or in the area of the spinous process 15, in accordance with the invention, a single incision gap 20 or 22 which makes it possible for the vertebral arch 12 or its vertebral arch sections separated by the incision gap 20 or 22 to be elastically/plastically widened so that further areas of the vertebra need not be exposed.

Creating the incision gap is not limited to any particular procedure. Thus, the incision gap may for example be produced using an ultrasonic osteotome, which provides a particularly gentle way of cutting through the bone substance down to the spinal canal 11. Damage to the connective tissue of the spinal cord is avoided here.

Alternatively, it is possible to work with fast rotating drills, with the last phase of the through-cut down to the spinal cord being preferably performed using a bone punch.

A further alternative is the use of what is known as the T-saw or Gigli saw, with which the incision gap is created starting from the spinal canal 11.

Figure 1B:
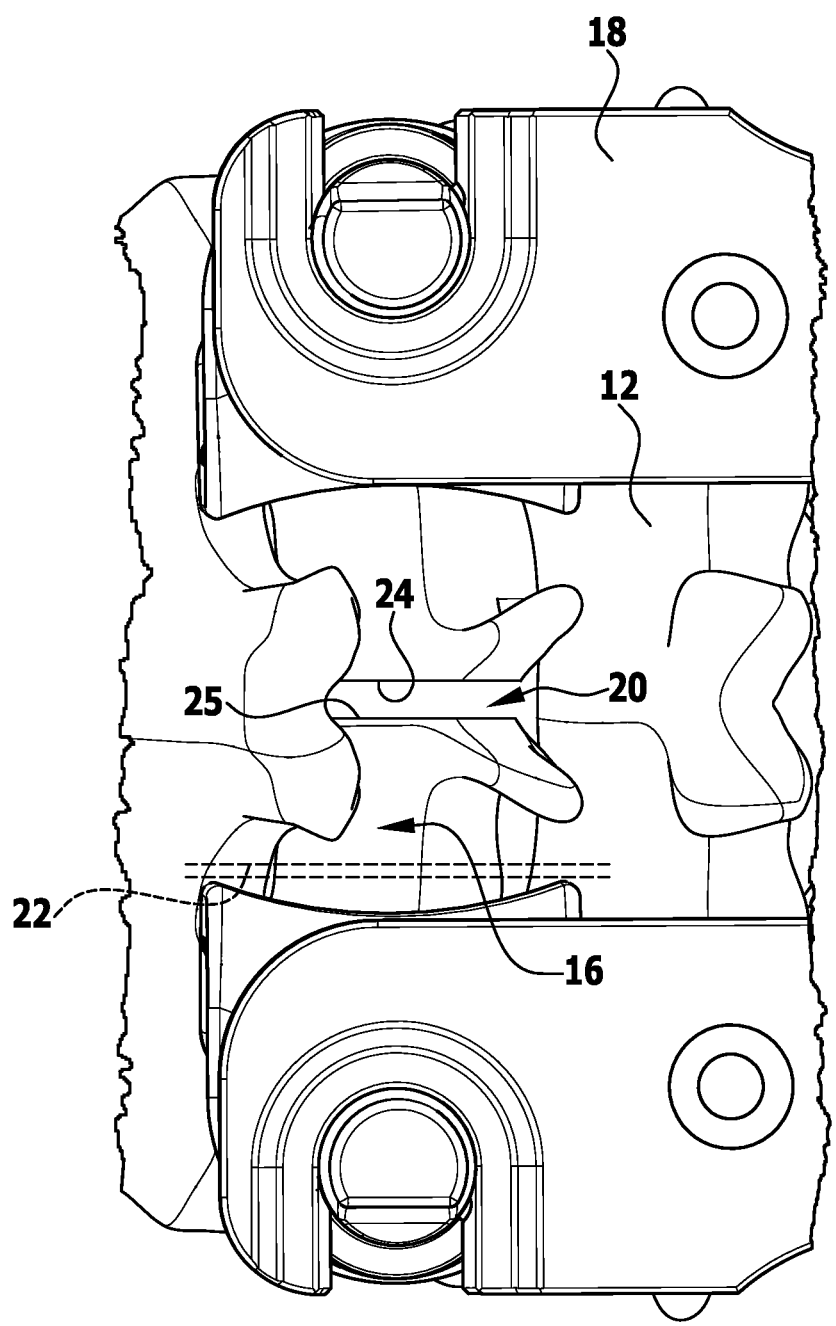

FIG. 1B depicts the vertebra 14 with the incision gap 20 produced in the spinous process. The alternative incision gap 22 in one of the laminae of the vertebral arch 12 is indicated in broken lines.

While the invention will be described hereinafter in terms of the incision gap 20 created in the spinous process, it will be apparent to the person skilled in the art that the procedure is analogously applicable to an incision gap 22 in the lamina.

The incision gap 20 has two incision faces 24 and 25 which are arranged parallel to each other in the state illustrated in FIG. 1B. The gap width that is present in this state depends on the technique used to create the incision gap and is for example about 1 mm or less when an ultrasonic osteotome is employed. With fast rotating drills, a width of the incision gap of about 2 mm to 3 mm is typically obtained.

Figure 2:
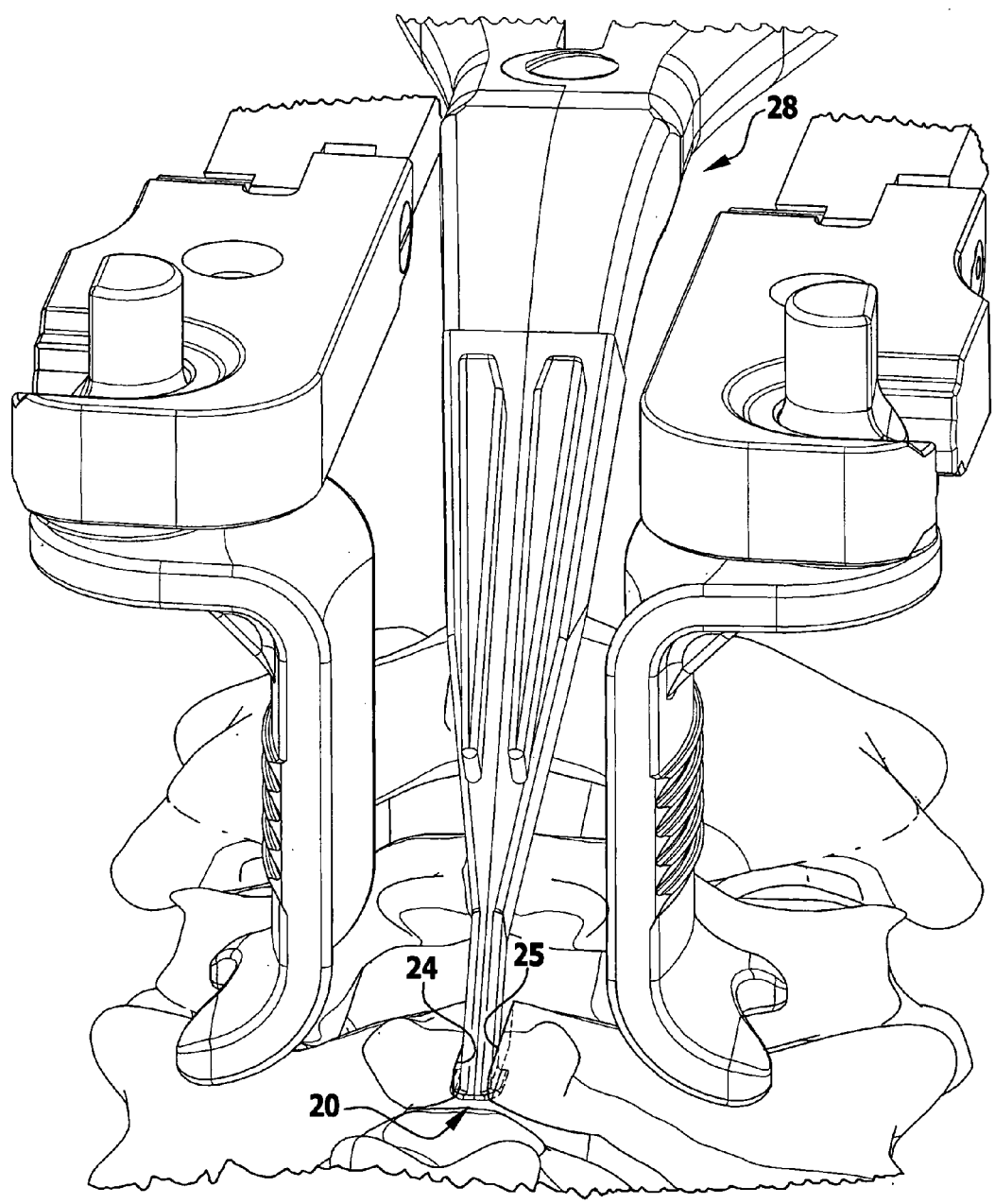
FIG. 2 shows the cervical vertebra of FIG. 1B with the incision gap in the process of being widened.

To elastically/plastically widen the incision gap 20, a distraction instrument 28 is used, which is dorsally inserted into the incision gap 20 as illustrated in FIG. 2. Preferably, the distraction instrument has a gap width indicating device and/or a force measuring device (both not shown) so that the gap width obtained can be read off and/or the force used for the widening can be applied in a metered manner. More preferably, the distraction instrument 28 has a latch element (not shown) which automatically fixes an expanded position of the distraction instrument once that position has been reached. Said latch element may also facilitate stepped widening of the incision gap.

Preferably, the distraction instrument 28 has an angled portion at its distal end so that the view is maintained even as the incision gap 20 is widened, and easy access for inserting the implant into the incision gap 20 is given.

Figure 3:
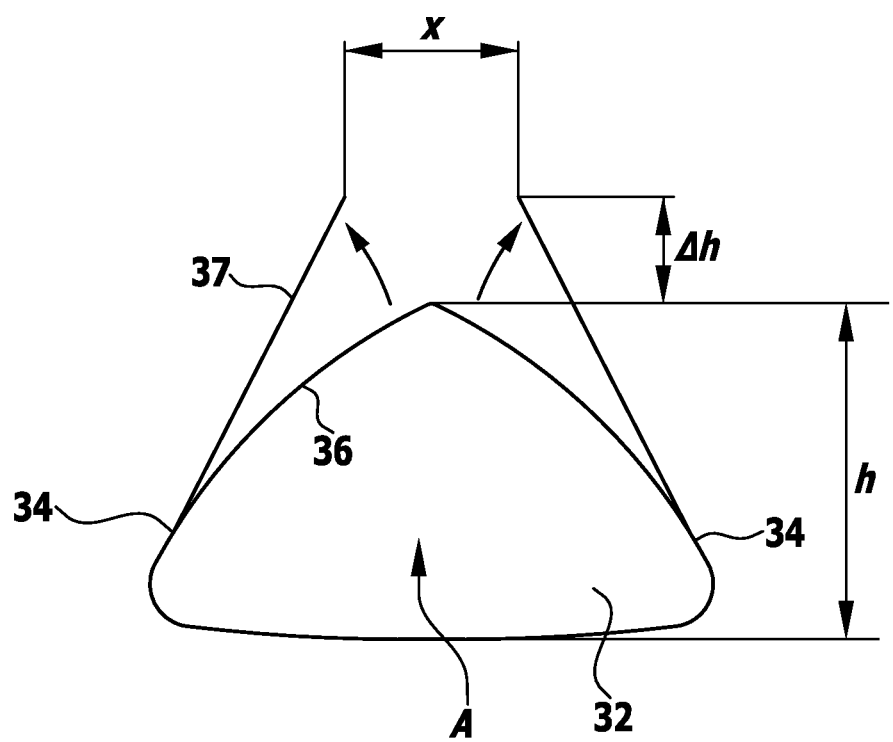
FIG. 3 is a schematic sectional view taken through a vertebral canal that has been elastically/plastically widened in accordance with the invention.

The outcomes in terms of widening the vertebral canal diameter or the vertebral canal area can be explained based on a simple model with reference to FIG. 3.

The starting point is a C6 vertebra with the parameters A=150.65 mm$^2$ and diameter h=11.5 mm, as indicated in FIG. 3. The calculations for a corresponding gap width x are based on the following assumptions:

- The shape of the spinal canal in the vertebra can be approximated by a curved triangle 32 as shown in FIG. 3.
- The fulcrum 34 of the vertebral arch sections lies in the area of what are known as the facet joints or pedicles.
- The sole elastic/plastic deformation of the sections of the vertebral arch 12 is assumed to occur in the area of the lamina, and for simplicity the lamina's arc length is assumed to be constant and the bending lines 36, 37 are simplified as curves.
- The vertebral body (not shown) and the junctions of the lamina and the vertebral body (pedicles) are assumed to be rigid.

In the calculation, the opening width (gap width), x, was increased in the range of 6 to 16 mm in 2 mm increments. The corresponding values for the growth in area, ΔA, or the growth in diameter, Δh, are listed in the following Table 1.

TABLE 1

| Gap width x | Growth in area ΔA | Growth in diameter Δh |
|---|---|---|
| 6 mm | 50.67 mm$^2$ | 3.79 mm |
| 8 mm | 63.30 mm$^2$ | 4.22 mm |
| 10 mm | 75.36 mm$^2$ | 4.53 mm |
| 12 mm | 86.72 mm$^2$ | 4.72 mm |
| 14 mm | 107.66 mm$^2$ | 4.99 mm |
| 16 mm | 126.84 mm$^2$ | 5.16 mm |

Figure 4A:
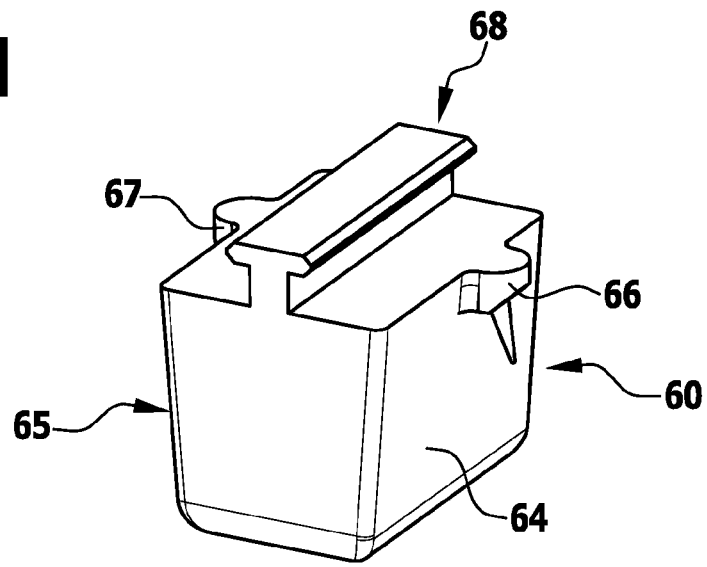
FIGS. 4A and 4B are two variants of a first embodiment of a first basic form of an implant constructed in accordance with the invention.
Figure 4B:
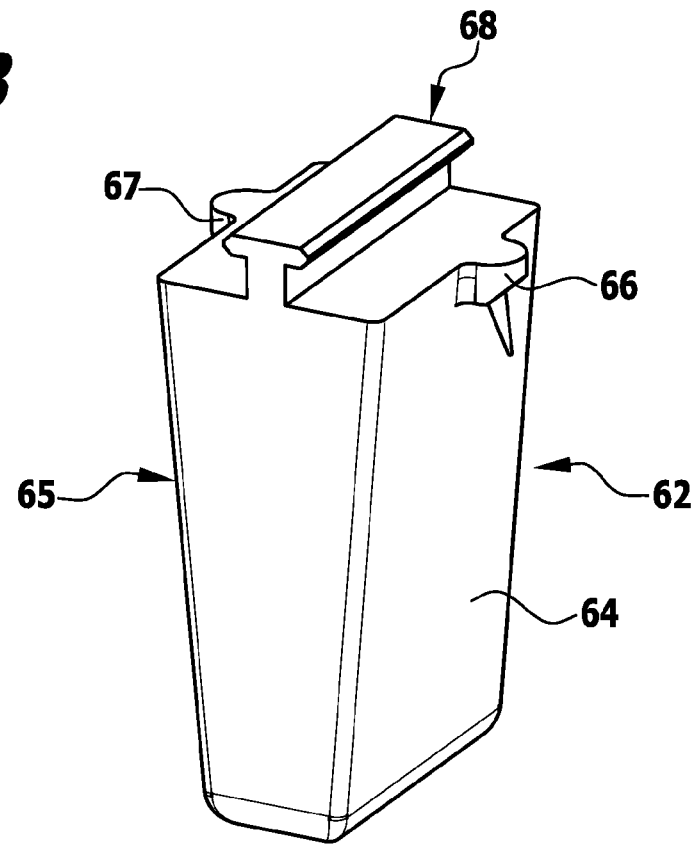

Once the widened incision gap 20 is ready to have an implant inserted therein, an implant body 60 or 62, as exemplified in FIGS. 4A and 4B, is preferably inserted into the incision gap 20.

The two implant bodies 60, 62 are both of solid configuration and are preferably made from an implant grade plastics material, in particular PEEK. The two implant bodies 60, 62 have contact faces 64, 65 that are inclined relative to each other and which, in the inserted state of the implant, are in contact over as large an area as possible with the incision faces of the incision gap. While the implant bodies 60, 62 are of wedge-shaped configuration when viewed in a front view, they may in fact be of substantially rectangular configuration in a side view.

At their upper ends in FIGS. 4A and 4B, which lie dorsally in the inserted state of the implant, the implant bodies 60, 62 have laterally projecting projections 66, 67 which can serve several functions:

On the one hand, the projections 66, 67 have the effect that the implant can be inserted into the incision gap only to the point at which the projections 66, 67 make contact with the bone substance and that displacement of the implant in a direction towards the spinal canal is inhibited also in the postoperative phase.

Furthermore, the projections 66, 67 in form-locking engagement with an instrument or with corresponding recesses in the bone substance can effect guidance of the implant body during insertion of the implant into the incision gap, thereby aiding in precise placement thereof.

Finally, the projections augment the dorsal area of the implant body and therefore facilitate the reception of holding elements, such as screws, spikes etc., which serve to fixate the implant in the widened incision gap.

Integrally formed on the implant bodies 60, 62 so as to protrude dorsally therefrom is a bar 68 undercut on both sides, serving as a grip element for improved handling of the implant during insertion and for correct positioning thereof.

Figure 5:
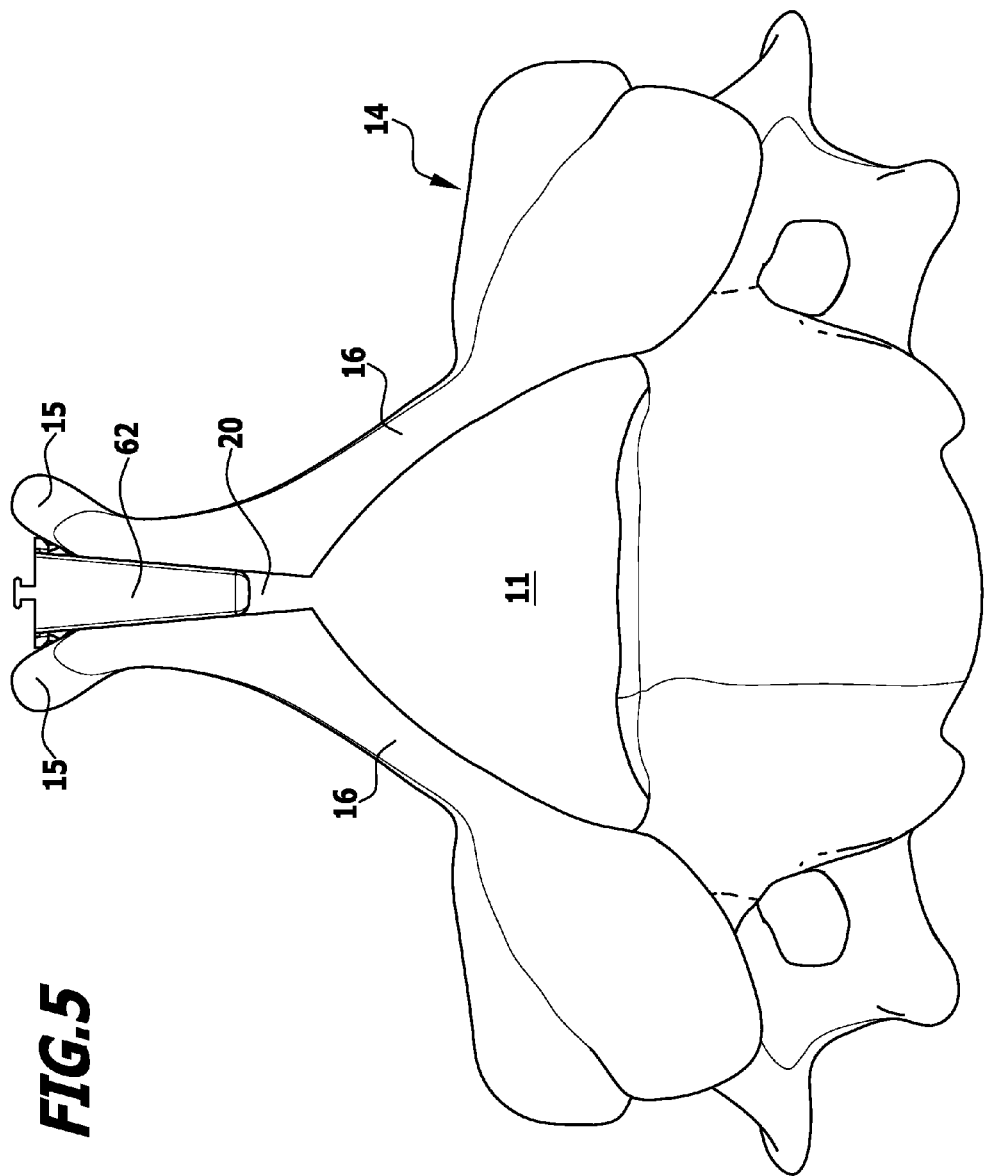
FIG. 5 is a side view of the cervical vertebra of FIG. 1B with the incision gap in a widened condition and having inserted therein an implant of FIG. 4B constructed in accordance with the invention.

FIG. 5 depicts the implant body 62 in its final position in the incision gap 20. In this example, the height of the implant body 62 is selected such that, in the inserted state, it does not quite extend down to the spinal canal with its ventrally located end so that an extra volume is left there for decompression of the spinal cord. In this preferred example, the angle at which the contact faces are inclined relative to each other in the shape of a wedge is about 10°.

FIG. 6 is a further exemplary embodiment of an implant body 80 constructed in accordance with the invention, shown in perspective, top and front views and in the implanted state (when seen in a top view). Again, the implant body 80 takes the shape of a wedge having contact faces 82, 83 that are inclined relative to each other and which, in the inserted state, are in contact over a large area thereof with the incision faces of an incision gap.

Preferably, said implant bodies 80 have at their contact faces semi-cylindrical projections 84, 85 which extend over almost the entire height of the implant body 80. Therefore, the correspondingly prepared incision gap has formed therein complementary grooves (not shown here) which guide the implant when it is being inserted. Where the grooves are used only for guiding the implants, they preferably do not extend all the way down to the vertebral canal so that a stop with which the projections 84, 85 come into contact results in the bone material of the incision faces, for insertion of the implant 80. This prevents overly deep insertion of the implant bodies 80 into the incision gap or future displacement of the implant body 80 in a direction towards the spinal canal, causing compression there.

Figure 6A:
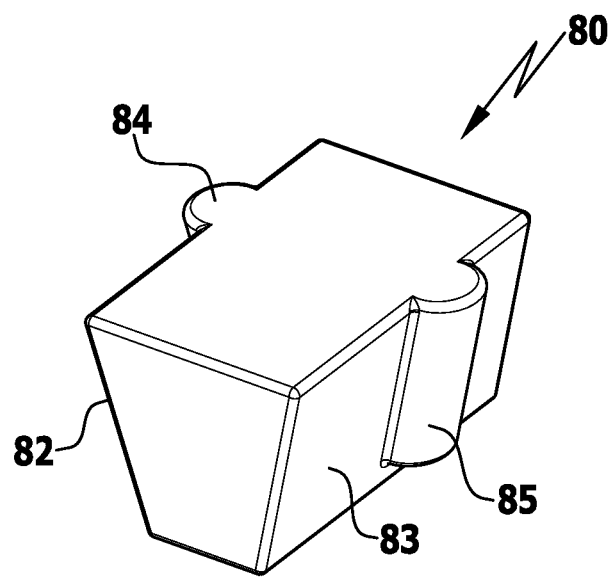
FIGS. 6A to 6D illustrate a second embodiment of the first basic form of the implant constructed in accordance with the invention, shown in perspective, side and top views and as inserted in an incision gap.
Figure 6B:
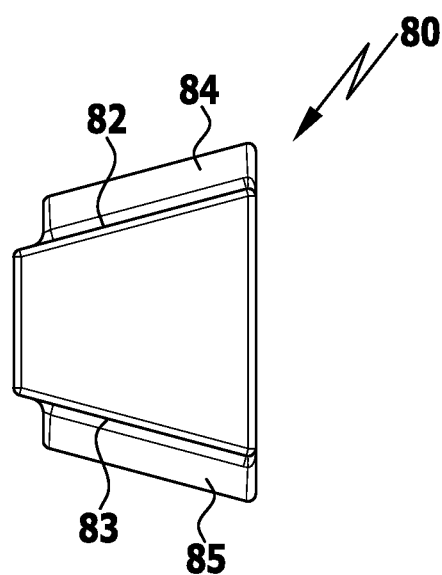
Figure 6C:
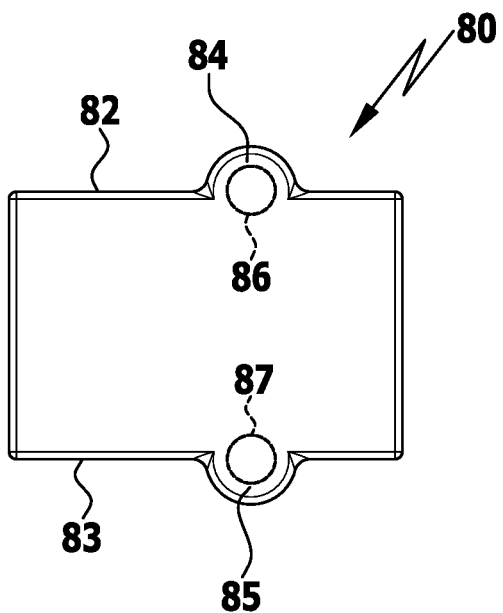

FIG. 6C illustrates a further configuration of the implant 80 schematically and in broken lines. Thus, the implant body 83 may have provided therein bores 86, 87 serving the insertion of fasteners, such as dowels, bolts and screws, as will be described in more detail below.

The projections 84, 85 allow for the bore openings in the implant body 83 to terminate dorsally at a larger distance from each other, which results in higher mechanical loadability of the implant and, moreover, simplifies the use of the fasteners.

Figure 6D:
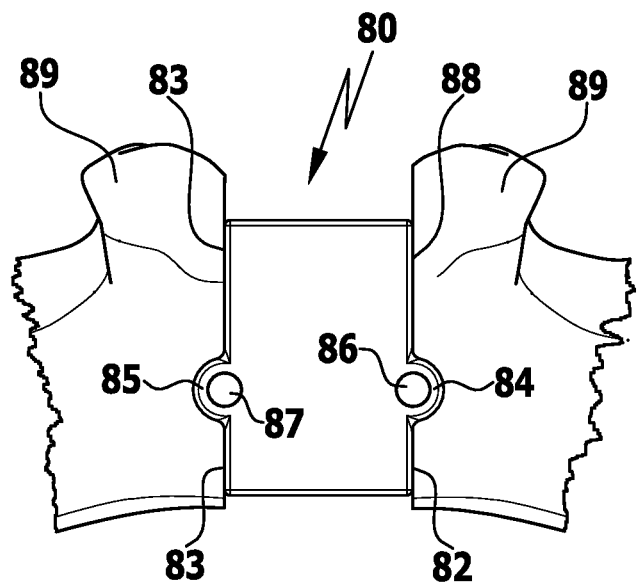

FIG. 6D shows the implant 80 as inserted in an incision gap 88. This view makes apparent the purpose of the projections 84, 85 being arranged in an off-centre position relative to the sagittal direction of the implant body 80: the corresponding recesses in the incision gap of the vertebral arch can, at least to a considerable extent, be arranged outside of the split spinous process 89 so that there results not only less intervention in the bone substance when forming the recesses, but it also makes easier the insertion of fasteners into the bores 86, 87.

Figure 7A:
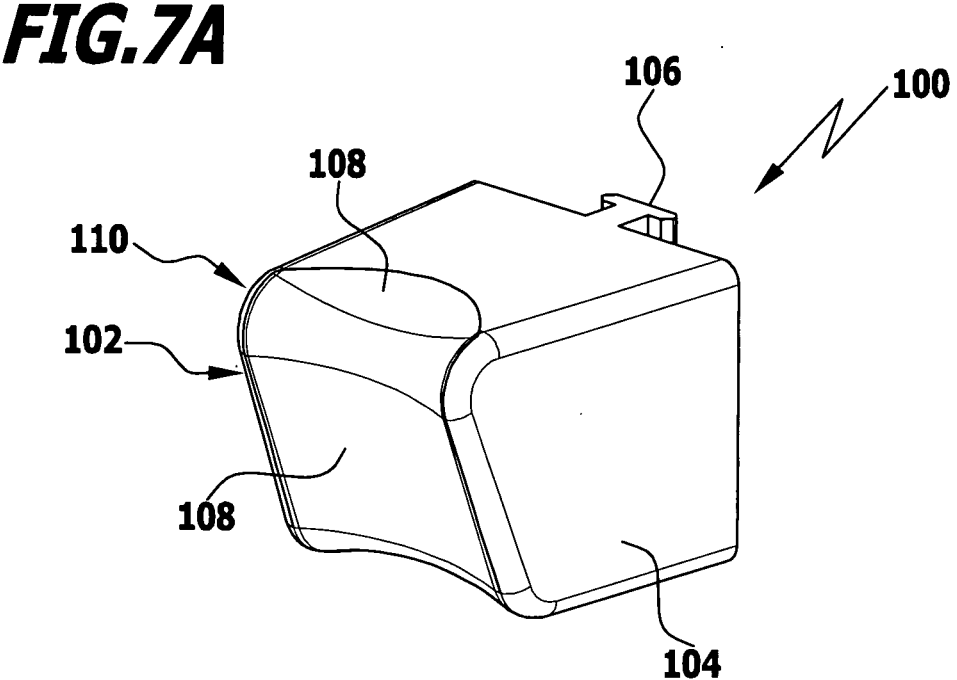
Figure 7B:
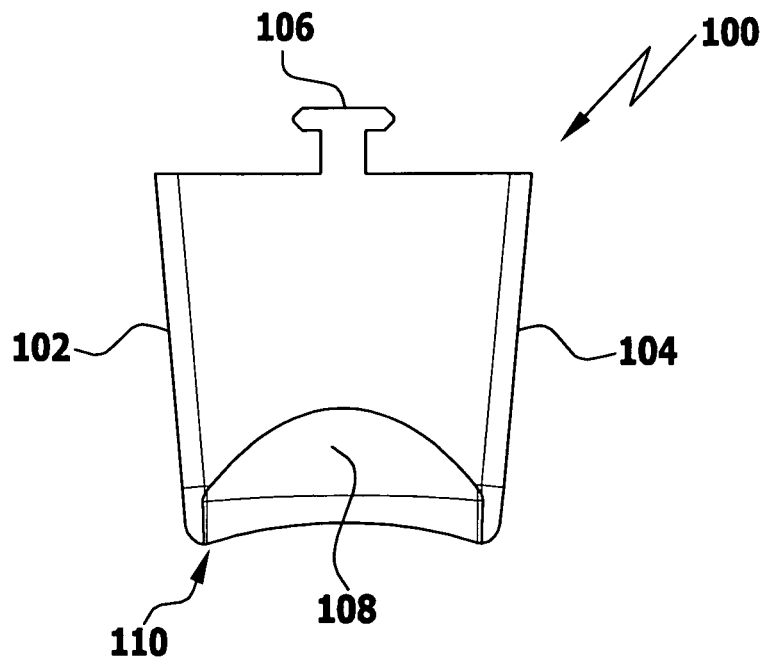

More particularly, FIGS. 7A and 7B show the detailed configuration of a preferred implant 100 constructed in accordance with the invention and which, like the previously discussed preferred implant bodies, has contact faces 102, 104 which are oriented relative to each other in the shape of a wedge and which, in the inserted state in the incision gap, make contact with the incision faces thereof. At its dorsal end, the implant has integrally formed thereon a grip bar 106 which allows it to be inserted precisely into the incision gap.

On its ventral side, the implant body 100 has an indentation 108 which extends around the ventrally projecting edge 110 and allows a further increase of the space available on the spinal canal side and therefore further decompression of the spinal cord. This arrangement on the implant body 100 side allows for an additional gain in space for the spinal canal which could otherwise only be achieved by substantially greater spreading apart of the vertebral arch.

FIGS. 7C to 7F illustrate further variants of the implant 100 constructed in accordance with the invention and shown in FIGS. 7A and 7B.

FIG. 7C shows an implant 120 having one, and preferably two, through-openings 122, 124 which are arranged parallel to the sagittal plane and which allow the implant to be sutured to the spinous process.

FIG. 7D shows an implant 126 comprising an implant body that is longer than the implant of FIG. 7C, and this allows additional bores to be provided so that parts of the spinous process that may have broken off can be additionally fixed to the implant. Although in this view a total of four bores 127, 128, 129, 130 is shown, one bore or through-opening each at the distal and proximal, or ventral and dorsal, end may in a simpler case be sufficient to ensure this additional benefit.

Figure 7E:
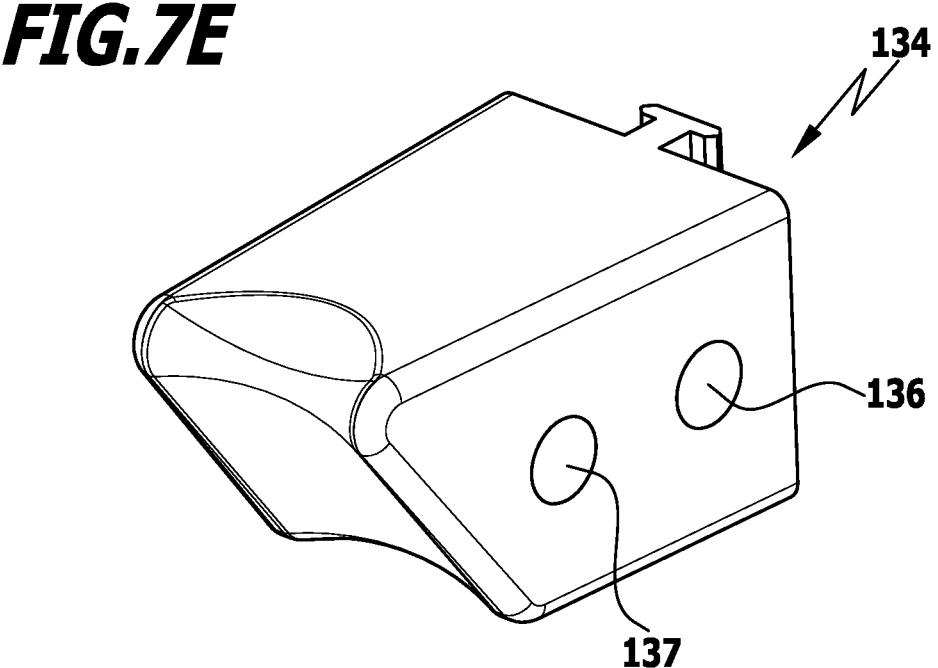

FIG. 7E is an alternative embodiment to FIG. 7C, showing an implant 134 in which the through-openings 136, 137 for suturing the implant are arranged transversely to the sagittal plane.

Figure 7F:
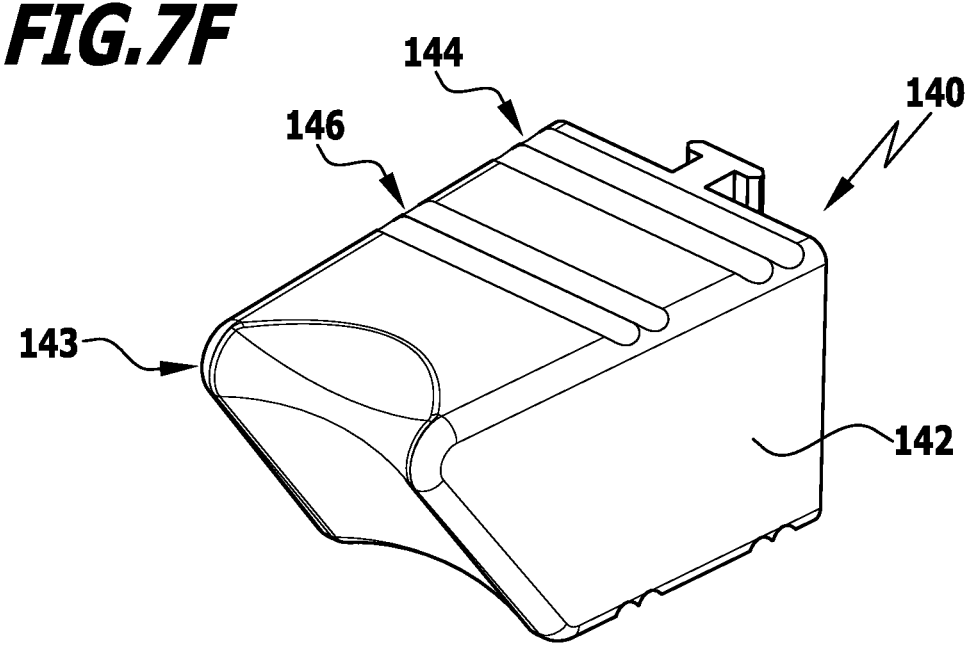

FIG. 7F shows a further alternative of an implant 140 capable of being fixated by use of suture thread. Here, the implant 140 has, in its surfaces transverse to the contact faces 142, 143, notches 144, 146 which guide and retain the thread(s) during suturing so that the thread(s) (not shown) cannot slip off when under the action of transverse forces.

Figure 8A:
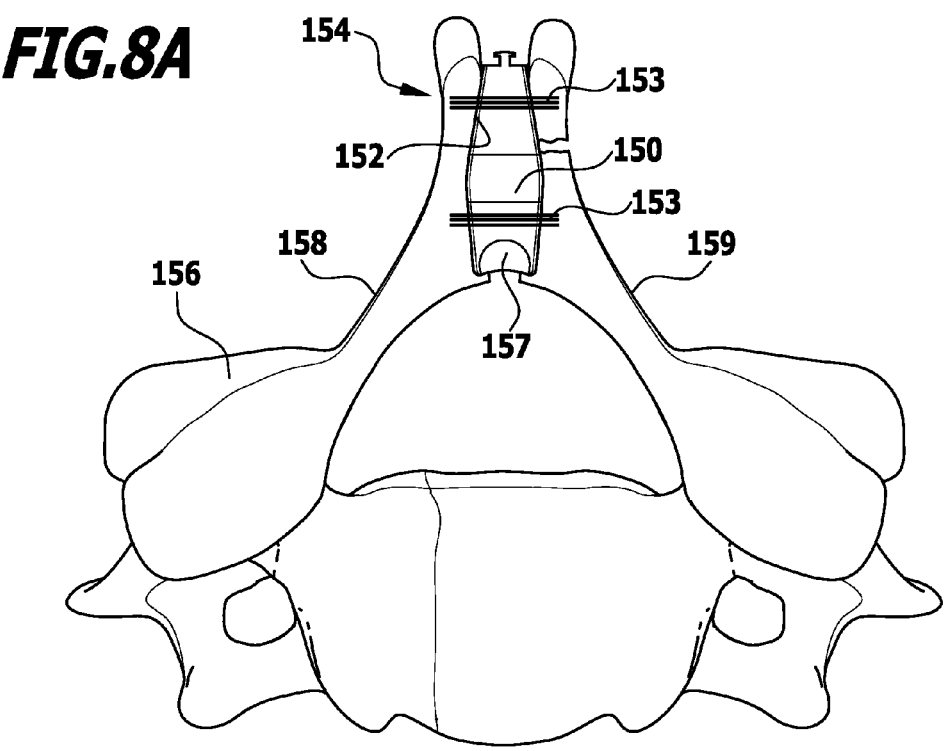
FIGS. 8A and 8B show a fourth embodiment of the first basic form of the implant constructed in accordance with the invention.
Figure 8B:
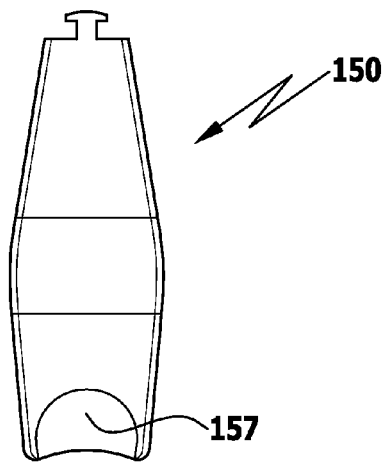

FIGS. 8A and 8B show a further variant of the implant 100. In this variant, the implant 150 has a larger height, which may for example be twice the height of the implant body 100, and preferably takes the shape of a double wedge. In the inserted state in an incision gap 152 of a split spinous process 154 of a vertebra 156, the ventrally arranged part, whose configuration corresponds essentially to that of the implant 100 as described in conjunction with FIGS. 7A and 7B, is positioned in the area of the incision gap of the lamina that is adjoined by the vertebral arch sections 158, 159. Correspondingly, the ventrally arranged part has an indentation 157. The dorsally arranged part is arranged between the parts of the split spinous process 154.

This variant of the implant 150 is advantageous in that for example a fractured piece of the spinous process 154 can be re-tethered thereto so that the fractured piece can grow back together. This also makes for a better surgical outcome from a cosmetic point of view.

FIG. 8A schematically shows the implant 150 as fixated to the spinous process or the lamina via suture threads 153 in the incision gap 152.

Figure 9:
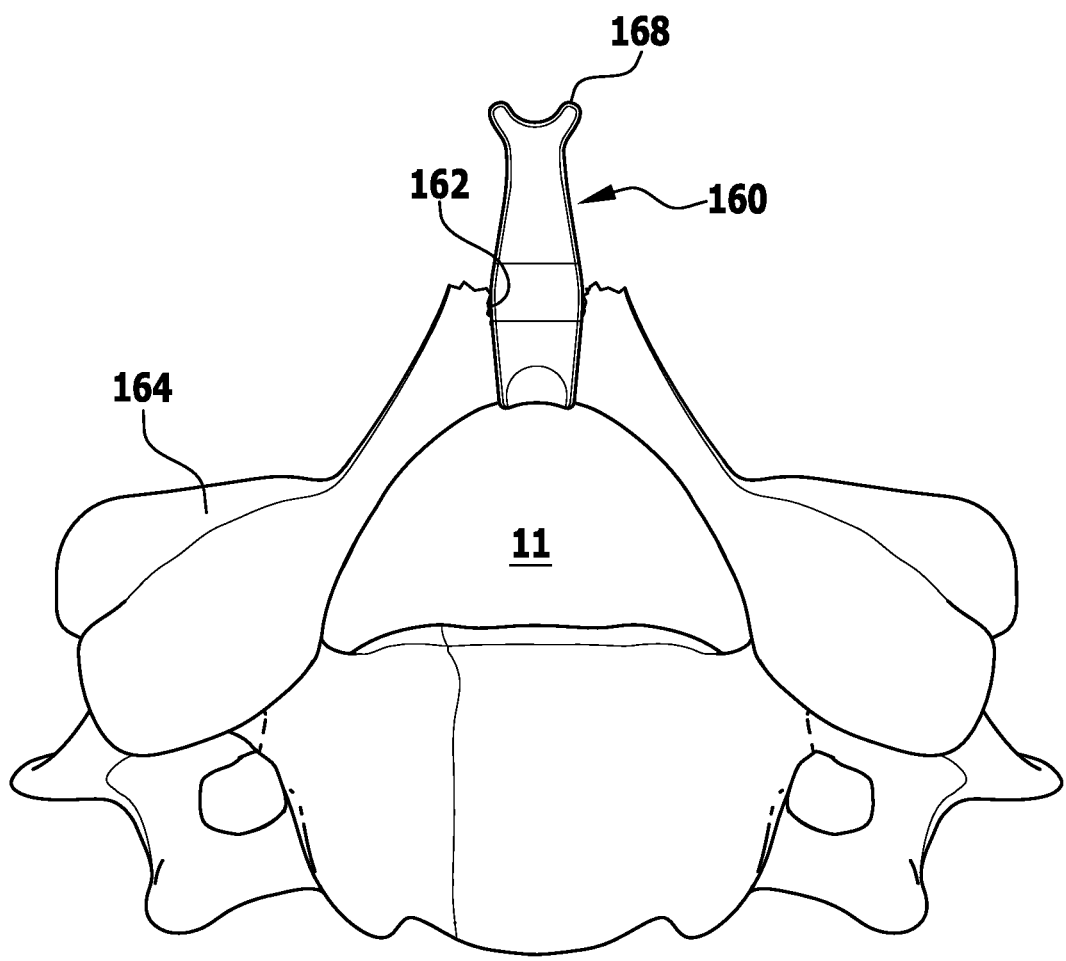
FIG. 9 shows a fifth embodiment of the first basic form of the implant constructed in accordance with the invention, inserted in an incision gap.

Developed from a similar point of view, the implant 160 of FIG. 9 may be used in operations in which the spinous process needs to be partially removed. FIG. 9 shows the implant 160 inserted in the incision gap 162 of a vertebra 164. The posterior end 168 (dorsal) of the implant body 160 replicates the pre-operative shape of the spinous process, thus achieving a cosmetically satisfactory result after surgery despite the removed parts of the spinous process. Furthermore, this embodiment of the implant affords the possibility of re-attaching detached muscles.

Figure 10A:
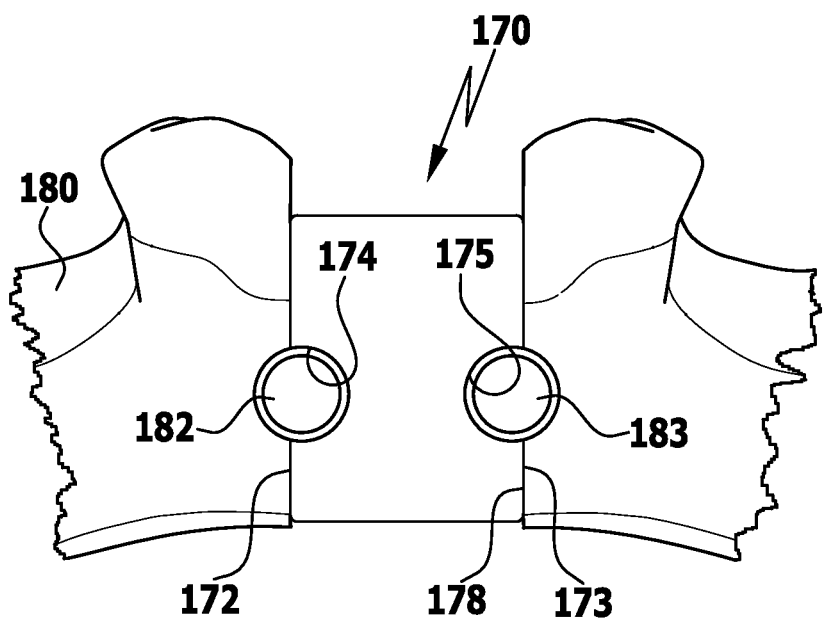
FIGS. 10A and 10B are top and sectional views of a first embodiment of a second basic form of the implant constructed in accordance with the invention, shown as inserted in an incision gap.
Figure 10B:
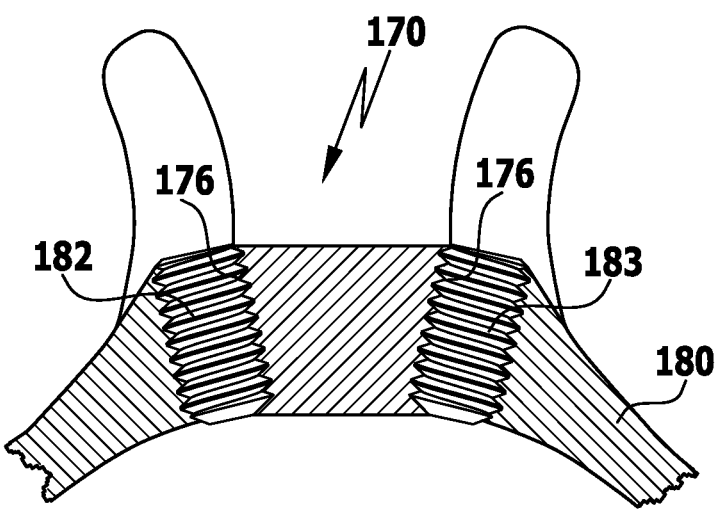

FIGS. 10A and 10B depict an implant 170 constructed in accordance with the invention which differs from the previously described basic form of an implant constructed in accordance with the invention in that the contact faces 172, 173 arranged in the shape of a wedge have formed thereon channel-like recesses 174, 175 which are of substantially semi-cylindrical design in the embodiment of FIG. 10 and have an internal thread 176 cut into them.

The incision gap 178 of the vertebral arch 180 is formed with complementary recesses of semi-cylindrical shape at the incision faces thereof so that with the implant 170 inserted in the incision gap 178, essentially cylindrical openings are first present.

Then, screw bolts 182, 183 are threaded into these cylindrical openings, with the screw bolts being guided by the internal thread 176, which is already present in the implant 170. On the recess side of the incision faces of the incision gap 178, the screw bolts 182, 183 cut their own thread as they are screwed in, with the advantage that in addition to the form-locking engagement of the thread a force-locking engagement is achieved which holds the screw bolts 182, 183 in their final screwed-in state also on a long-term basis.

The material of the screw bolts 182, 183 is preferably PEEK, and the material of the body of the implant 170 is preferably also PEEK so that undisturbed observation of the widened spinal canal is possible in follow-up examinations using MRI.

Figure 11:
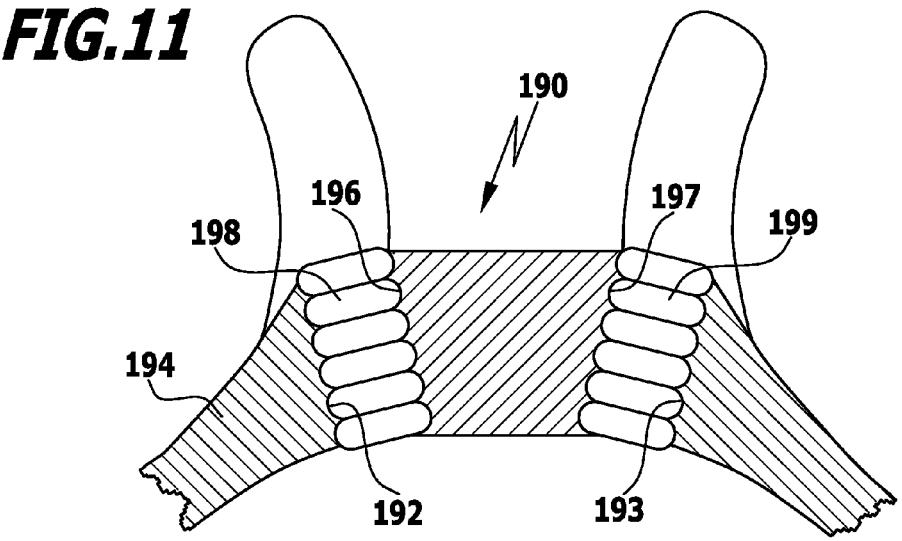
FIG. 11 is a sectional view of an implant in accordance with a second embodiment of the second basic form.

FIG. 11 shows a second embodiment of the second basic form in the form of the implant 190, likewise inserted in an incision gap 192 of a vertebral arch 194. As described in conjunction with FIGS. 10A and 10B, the implant 190 has at its contact faces semi-cylindrical recesses so that again essentially cylindrical hollow spaces result in the inserted state of the implant 190 in the vertebral arch 174. Dowel elements 198, 199 are then inserted into these hollow spaces, formed by the channels 192, 196 and 193, 197, said dowel elements 198, 199 being made of a material which can be plastified for a short length of time by the input of energy, such as ultrasound, heat, HF etc., and can thus adapt to the conditions of the surfaces of the incision gap of the vertebral arch 194 on the one hand and to the surfaces of the recesses 196, 197 of the implant 190. A form-locking connection is thereby achieved.

In this regard, the recesses 192, 193 in the incision faces of the incision gap of the vertebral arch 194 are preferably provided with notches or a thread so that a stronger form-locking engagement is achieved. Exactly the same applies to the recesses 196, 197 on the implant 190 side.

Figure 12A:
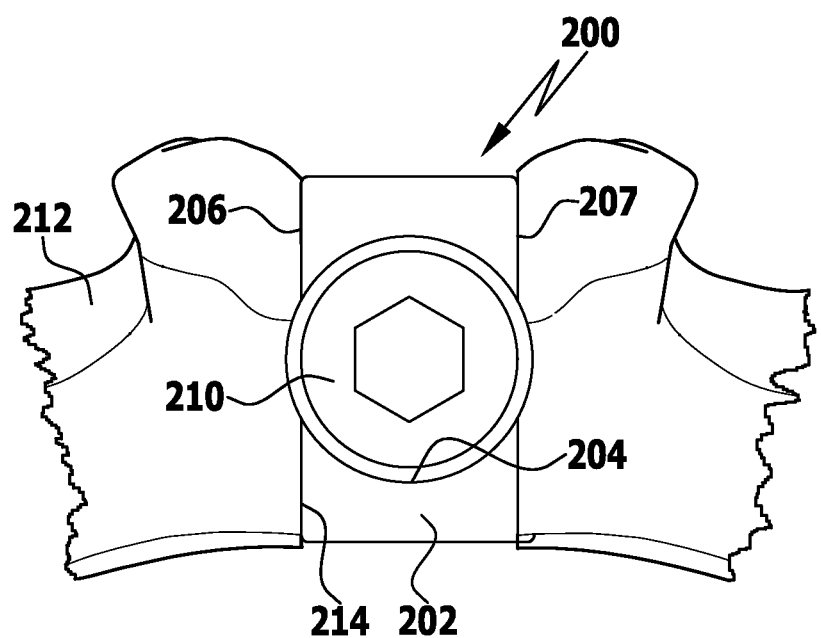
FIGS. 12A and 12B are a top view and a sectional view of a first embodiment of a third basic form of an implant constructed in accordance with the invention, shown as inserted in an incision gap.
Figure 12B:
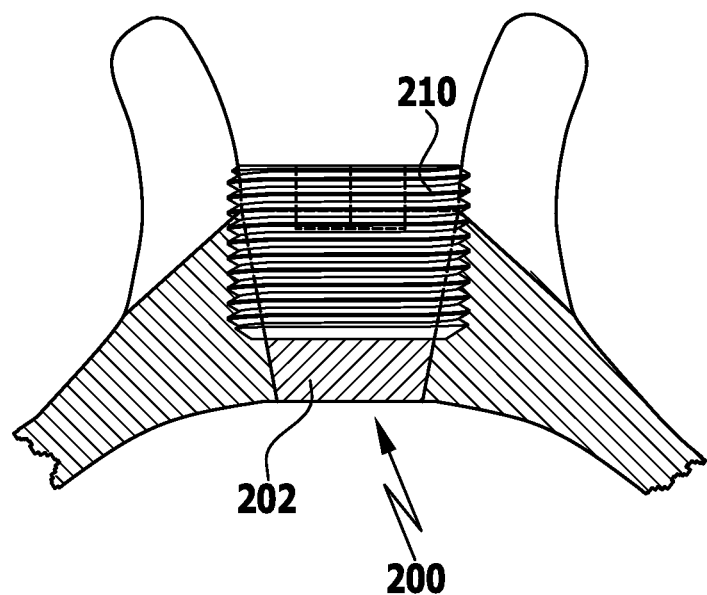
Figure 13A:
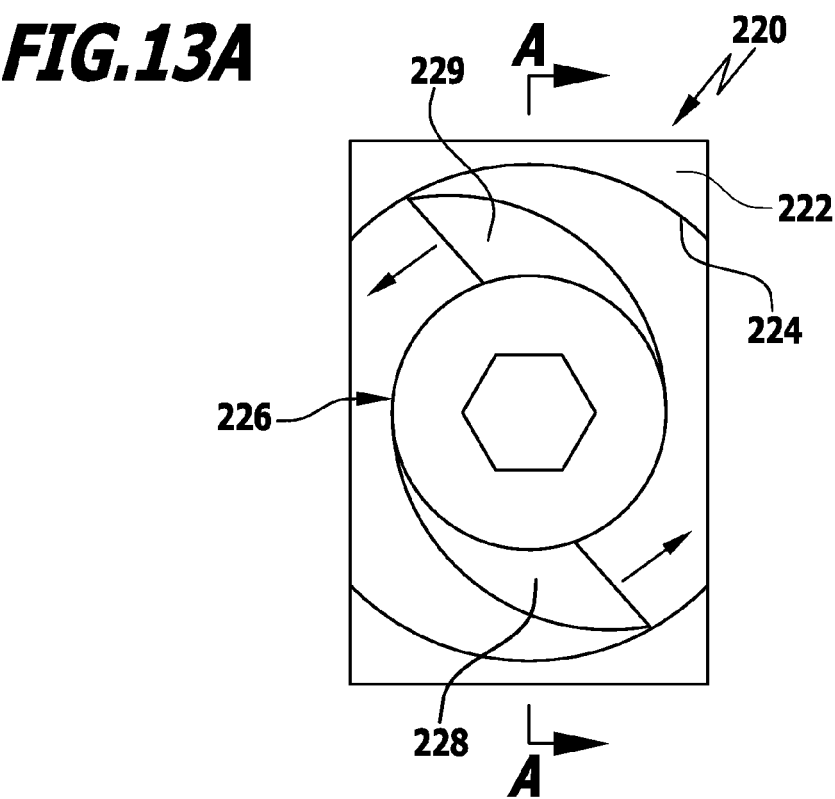
FIGS. 13A and 13B show a second embodiment of the third basic form of an implant constructed in accordance with the invention.

FIGS. 12 and 13 show a third basic form of the implant constructed in accordance with the invention; first referring to FIGS. 12A and 12B, this is shown in the form of an implant 200.

Here, the implant body 202 has a cutout 204 which is arranged as a blind hole in the dorsal end region of the implant body 202 and preferably has an internal thread formed on its walls.

The diameter of the blind hole 204 is larger than the distance between the contact faces 206, 207 of the implant body 202 at the dorsal end region thereof. This allows a locking element 210 to be introduced which may be in the form of a bone screw for example. With the implant 200 inserted in a vertebral arch 212 or in the incision gap 214 thereof, the central bone screw 210 having a diameter that is larger than the distance between the contact faces 206, 207 can be screwed into the implant body 202, wherein the outer circumference of the locking element 210 or the thread thereof located there cuts its own way into the bone substance of the vertebral arch 212, thus providing for a form-locking engagement between the implant 200 and the bone substance of the vertebral arch 212. If the diameter of the locking element 210 is considerably larger than the distance between the contact faces 206, 207 of the implant body 202 at the dorsal end region thereof, as it is shown in FIGS. 12A and 12B, it is to be recommended that prior to inserting the implant 200, the incision gap 214 be prepared by forming recesses on its incision faces so that excessive compression of the bone substance or excessive application of force thereto arising from the turning-in of the locking element 210 during fixation of the implant 200 in the incision gap 214 is avoided and the contact faces 206, 207 continue to make contact with the incision faces of the incision gap.

FIG. 13 shows an implant 220 the basic principle behind which is similar to that of the implant 200 from FIGS. 12A and 12B. The implant 220 has in its implant body 222 a blind hole 224 which again preferably has an internal thread formed therein.

Figure 13B:
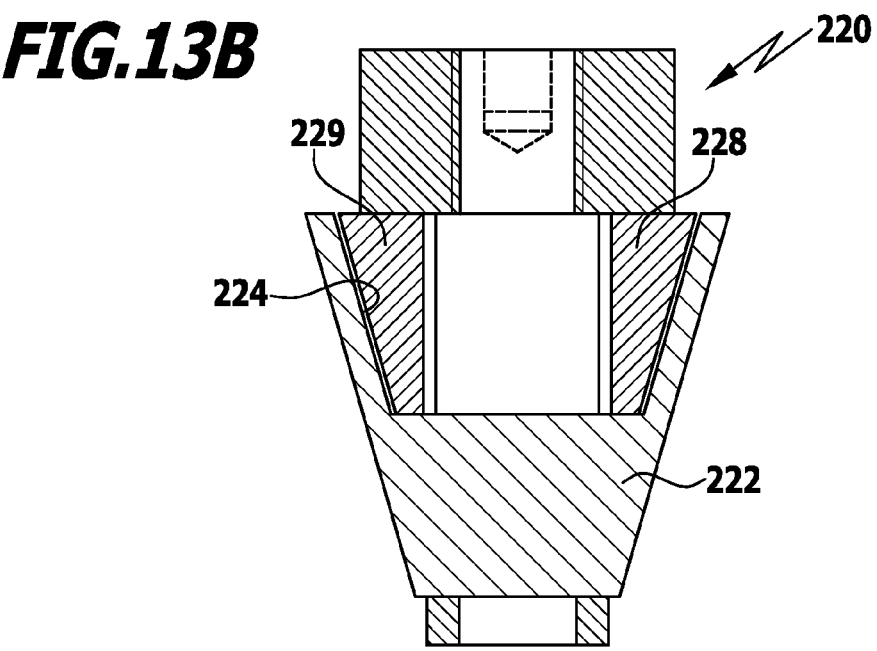

Rotatably held in the blind hole 224 is an anchoring element 226 which has on the outer circumference of its cylindrical base body two wings 228, 229 which, upon rotary movement of the locking element 226, press their way into incision faces of an incision gap of a vertebral arch that are arranged adjacent to the implant body 222. FIG. 13B is a sectional view of the implant taken along line A-A of FIG. 13A.

Figure 14:
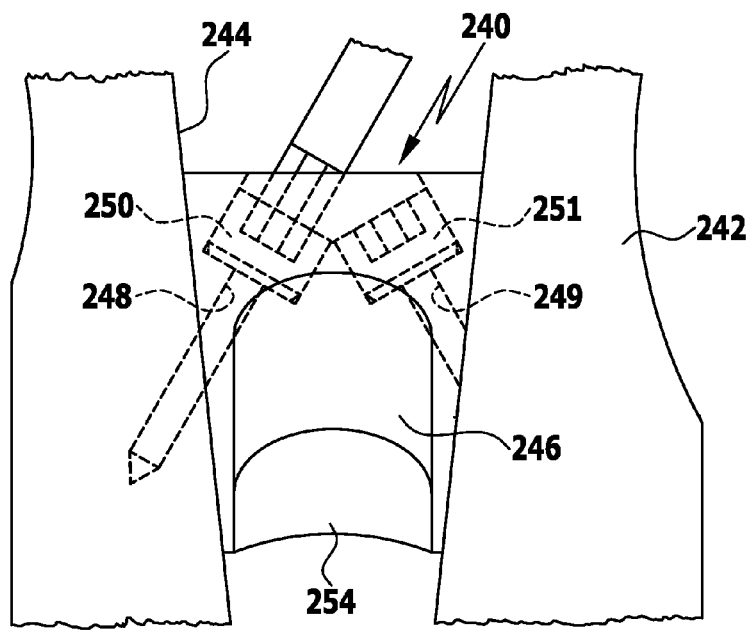
FIG. 14 depicts a variant of the third embodiment of the first basic form of an implant constructed in accordance with the invention, in the implanted state.

FIG. 14 is an implant 240 constructed in accordance with the invention, shown as inserted in the incision gap 244 of a vertebral arch 242 with spinous process. In terms of its configuration, the implant body corresponds essentially to the implant body 100 of FIGS. 7A and 7B; however, the implant body 246 has two through-bores 248, 249 which are at an acute angle to the contact faces of the implant 240 and extend from the dorsal end region of the implant to the respective contact face.

Inserted in these through-bores 248, 249 are pins 250, 251 which exit from the bores 248 and 249 respectively at the contact faces of the implant body 246, and at this point they then penetrate the surrounding bone substance of the vertebral arch 242.

While pins having a threaded section at the tip thereof may be used so that the pin cuts its own way into the bone material as it is turned in, it is also possible to use smooth pins which are pressed into the bone material by gently striking them. It is however preferred that, when inserting the pins, the implant be held in place in its correct position in the incision gap 244 so that it cannot become displaced in a ventral direction, i.e., in a direction towards the spinal canal.

The pins 250, 251 can be secured in the bores 248, 249 by way of securement means as are known per se for example from pedicle screw systems or cervical plate systems. Preferably, as illustrated in FIG. 14, the through-openings 248, 249 are formed with a dorsally expanded section so that at the transition to the ventral section of the through-openings 248, 249 a stop is formed which is then contacted by a head of the pin having a larger diameter so that the final position of the pin can also be predetermined in advance. As with the implant body from FIGS. 7A and 7B, the implant body 240 has on its ventral side, or its side adjacent to the spinal canal, an indentation 254 to thus create additional volume for the spinal canal.

FIG. 15 schematically shows a further implant 260 of the present invention which compared to the implant 240 of FIG. 14 uses the reverse principle for its fixation in the vertebral arch or the spinous process 262 thereof and the incision gap 264 thereof.

Figure 15A:
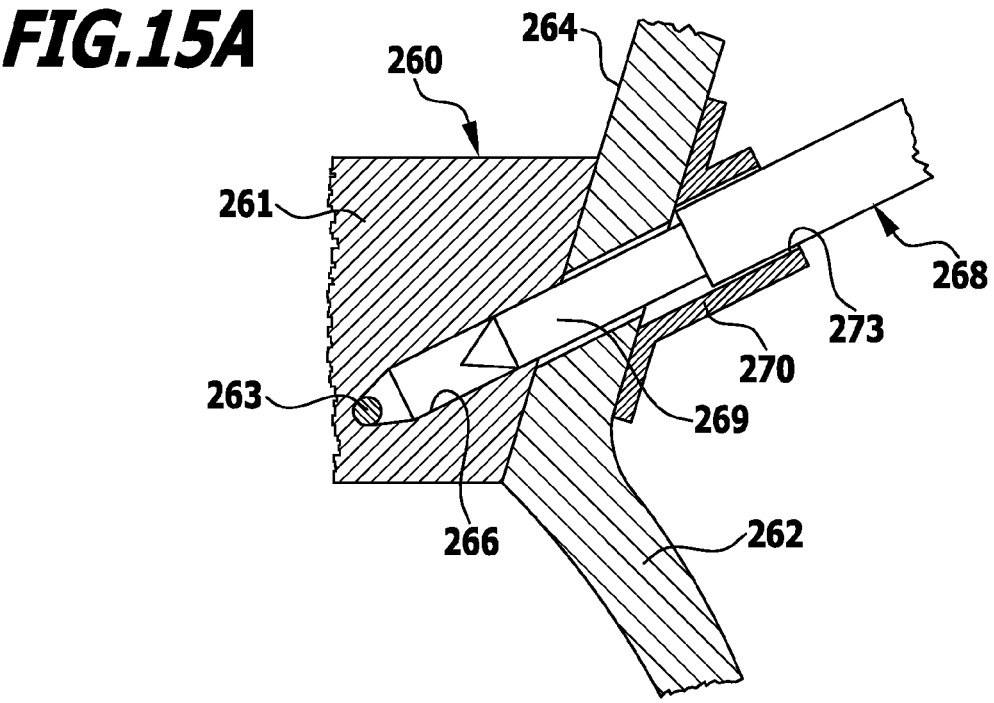
FIGS. 15A and 15B illustrate a variant of the third embodiment of the first basic form of the implant constructed in accordance with the invention, in the implanted state.

First referring to FIG. 15A, the implant 260 is shown as inserted in the incision gap 264. The muscles have been partially stripped away from the spinous process 262.

The implant 260 has integrally contained in its implant body 261 a tantalum marker in the form of a sphere 263 which in a radiographic image indicates the end point of a bore 266 created from the exterior.

A drilling tool 268 having a stepped drill bit 269 and a support plate 270 is placed into contact with the outer face of the spinous process 262, and the bore in the spinous process or lamina is created under radiographic viewing.

Figure 15B:
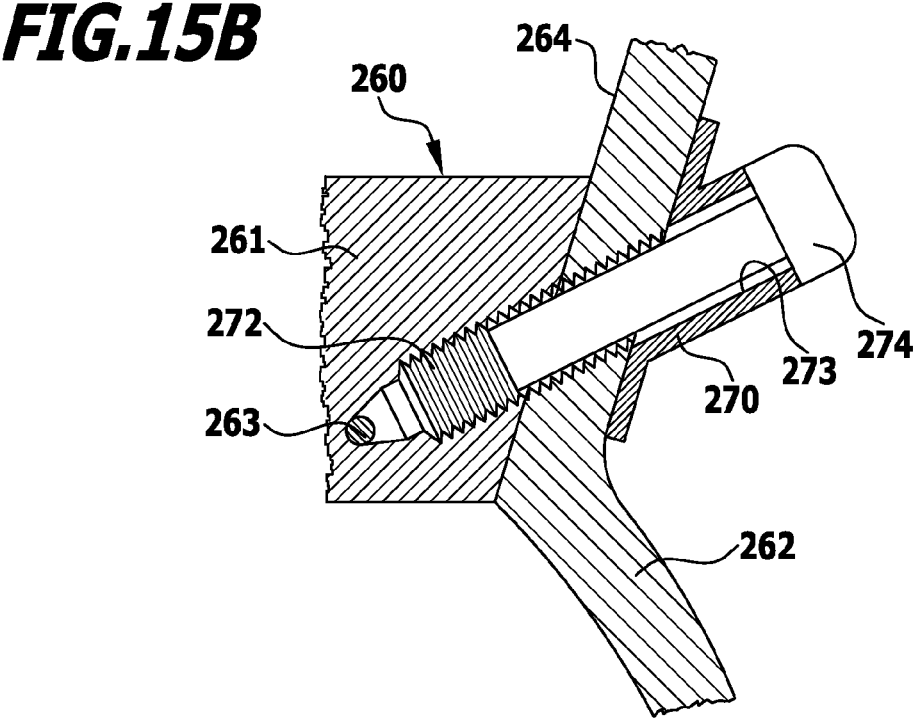

Subsequently, the drilling tool can be removed. As depicted in FIG. 15B, the support plate 270 can remain in place on the outside of the spinous process 262 so that its opening 273 continues to be aligned with the bore 266.

A fastening element 274, in particular a screw, is inserted through the opening 273 of the support plate 270 and screwed to the implant body 261. The threaded section 272 of the screw 274 comprises an undercut which cuts its own mating thread in the implant body 261.

In FIG. 16, the two variants A and B are further implants 280 and 300 respectively, constructed in accordance with the invention and shown as inserted in an incision gap 282 and 302 respectively of a vertebral arch 284 and 304 respectively. Common to both implants 280, 300 is the general mechanism for fixing the implants 280 and 300 respectively in the respective incision gap 282 and 302, in which anchoring elements are driven into the surrounding bone substance of the incision gaps 282 and 302 respectively via a sliding guide.

Figure 16A:
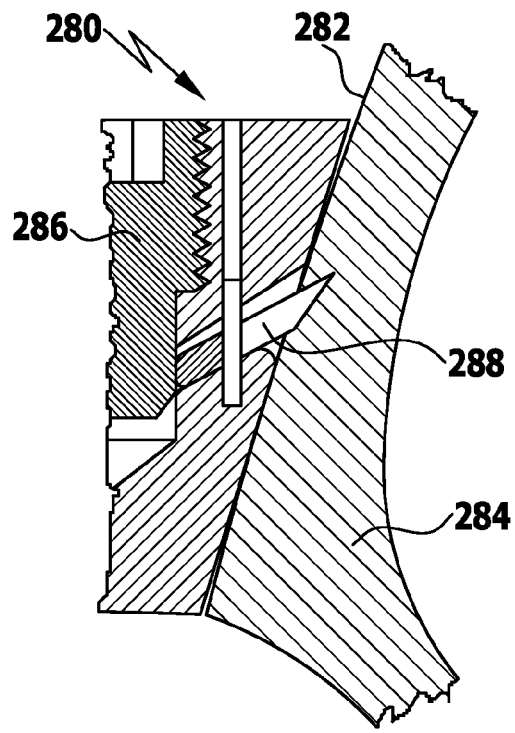
FIGS. 16A and 16B show two further variants of the third embodiment of the first basic form of the implant constructed in accordance with the invention, in the implanted state.

To this end, the implant 280 of FIG. 16A has an actuating element 286 which tapers towards the ventrally located tip thereof and thus forms a slide in order for a locking element 288 mounted for displacement in a lateral opening of the implant body 280 to be driven towards the outside, i.e., beyond the contact face of the implant 280, and thus allowed to penetrate the surrounding bone substance of the vertebral arch 284. The locking element 288 preferably has a sharp point so that it takes only a small amount of force to drive it into the spongious bone substance of the incision gap 282.

Figure 16B:
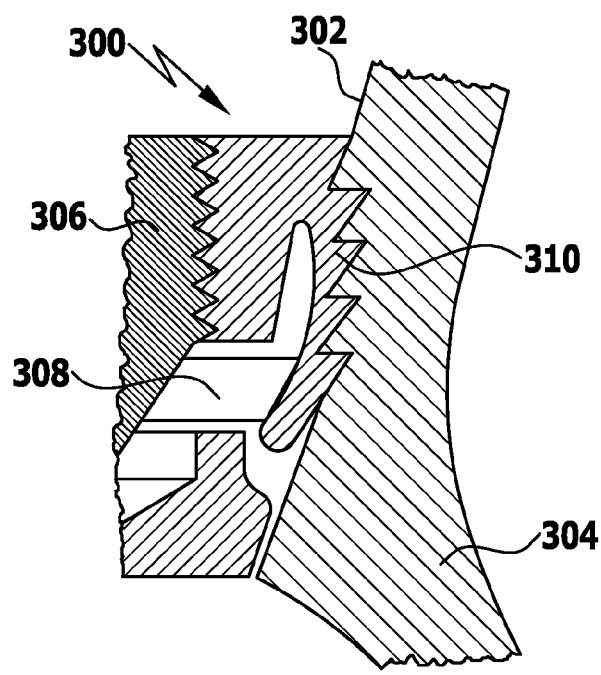

An alternative solution to the above is chosen in the embodiment of FIG. 16B in which, likewise, an actuating element 306 having a conically tapered tip forms a slide via which an anchoring element held for movement on the contact face of the implant 300 is driven into the surrounding spongious bone substance by way of a force transmission bolt 308. The anchoring element 310 can preferably be formed in one piece with the implant 300 and, in particular where the implant is fabricated from PEEK material, it can be held with sufficient movement capability on the implant body itself owing to the elastic properties of the PEEK material.

Figure 17A:
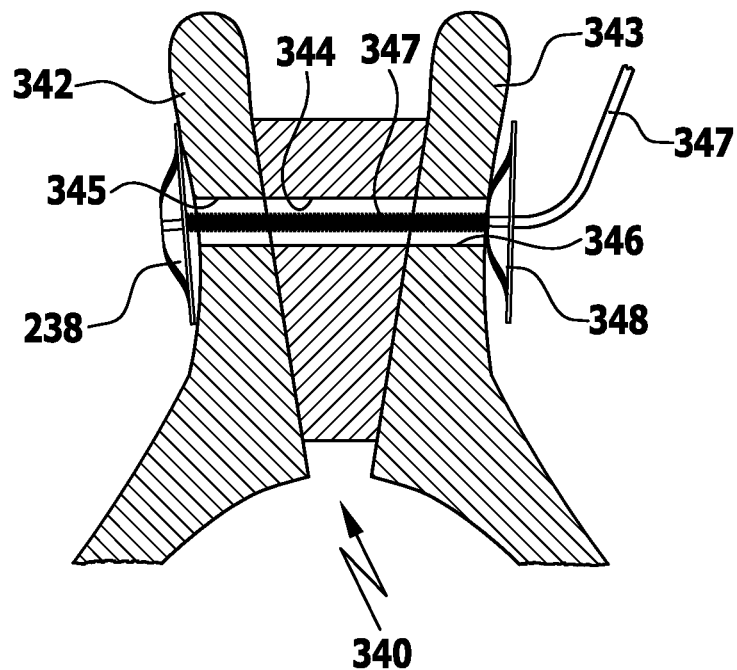
FIGS. 17A and 17B show a further variant of the third embodiment of the first basic form of the implant constructed in accordance with the invention, with an associated holding element.

FIG. 17A is a further variant of an implant 340 constructed in accordance with the invention, shown in the installed situation between the halves 342, 343 of a split spinous process.

The implant body 340 has a bore 344 which is arranged transversely to the longitudinal direction or depth of the implant and aligns with corresponding bores 345, 346 or cutouts in the spinous process 342, 343.

In the inserted state of the implant body 340 in the spinous process 342, 343, for example a wire segment 347 is then inserted through the bore 344 and the cutout 345, 346 and fixed at its free end by way of a holding element 348. The second free end of the wire segment 347 is also fitted with a holding element 348 as it is exemplified in FIG. 17B, viewed from above and from the side at an enlarged scale.

Preferably, the wire segment 347 has a structure which allows the holding elements 348 to be snap-fit thereto without a special tool so that after insertion of the wire segment 347 and the holding elements 348 fixed thereto, the wire segment 347 can be easily tightened and the holding elements 348 placed into contact with the outer faces of the spinous process parts 342, 343, thus securing the implant body 340 in the incision gap.

Figure 18:
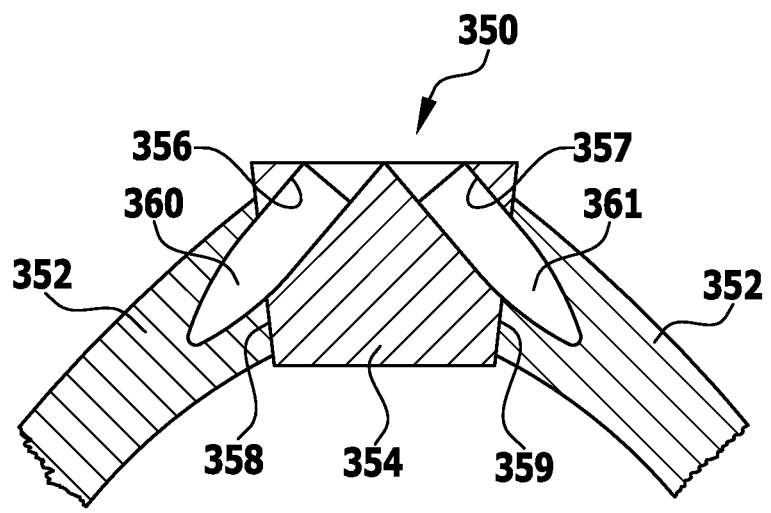
FIG. 18 is a sectional view of a further variant of the third embodiment of the first basic form of the implant constructed in accordance with the invention, in the implanted state.

FIG. 18 is a sectional view of the installed situation of an implant 350 constructed in accordance with the invention in the incision gap of a vertebral arch 352, wherein the implant body 354 has provided therein two bores 356, 357 which extend at an acute angle relative to the contact faces of the implant body 354, with which the latter contacts the incision faces of the incision gap of the vertebral arch 352. The bores 356, 357 extend from the dorsal surface of the implant body 354 and exit from the contact faces 358, 359.

When the implant 350 is fixated in the vertebral arch 352, sharp-pointed bolts 360, 361 are inserted in the bores 356, 357 and, in the installed state, protrude with their tip beyond the contact faces 358, 359, penetrating the surrounding bone substance of the vertebral arch 352.

The bolts 360, 361 can be configured in various ways. In accordance with one embodiment, the bolts 360, 361 may consist of a plastifiable material and are plastified for a short length of time when in the inserted state so that a form-locking connection results between the material of the bolts 360, 361 and the bone substance of the vertebral arch 352 surrounding them at their tips.

In accordance with another embodiment, the bolts are configured as what are known as spikes and are held in the implant body 354 and the adjoining portions of the bone substance of the vertebral arch 352 in a substantially force-locking engagement therewith.

Figure 19A:
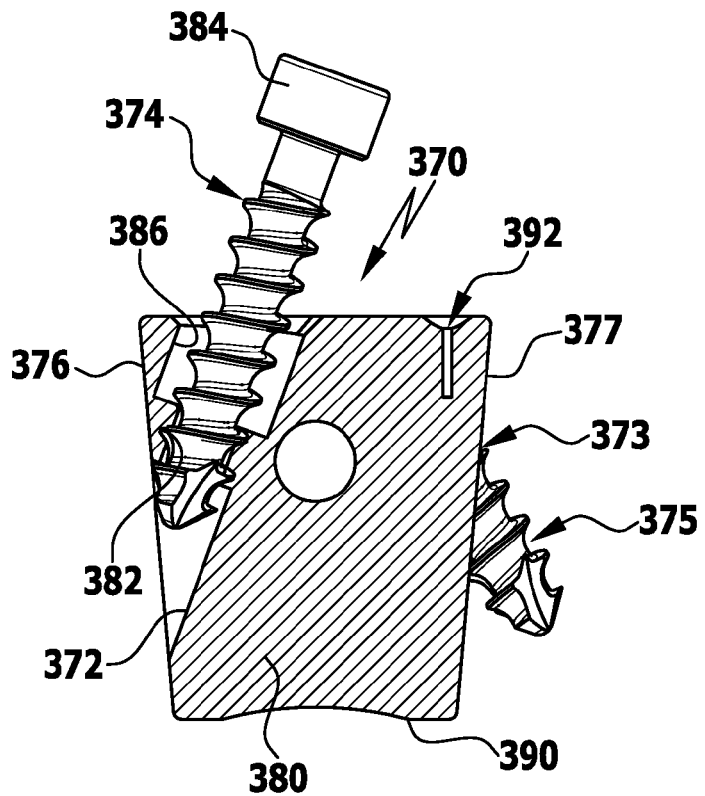
FIGS. 19A and 19B are sectional views of a further variant of the third embodiment of the first basic form of the implant constructed in accordance with the invention.
Figure 19B:
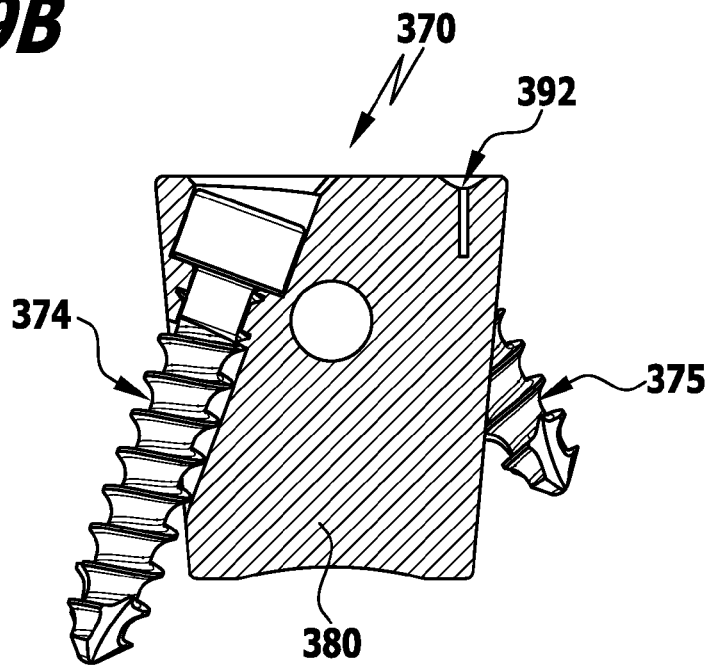

In accordance with a further variant of an implant 370 constructed in accordance with the invention, illustrated in FIGS. 19A and 19B, the bolts are configured as screw bolts 374, 375 which are screwed with their tip into the bone substance of the vertebral arch (not shown) that contacts the contact faces 376, 377 of the implant.

View A of FIG. 19 is a sectional view taken through the implant body 380 which—similarly to what has been described for FIG. 18—has two through-openings 372, 373 extending at an acute angle with respect to the contact faces of the implant body 380. Unlike with the implant 350 of FIG. 18, the two through-openings 372, 373 are arranged in staggered relation here; therefore, only the through-passage 372 shown as located at the front of the drawing is fully visible in views A and B of FIG. 19. Arranged in both through-openings 372, 373 are screw bolts 374, 375, of which the screw bolt 375 is already in the fully screwed-in position in the through-opening 373 and with its pointed end penetrates beyond the contact face into the bone substance of a vertebral arch (not shown here).

In the FIG. 19A view, the screw bolt 374 is shown as still in its initial position in which it is held in a form-locking manner by a short threaded section 382 forming part of the through-opening 372.

Once the implant body 380 has been inserted into an incision gap of a vertebral arch, the two screw bolts 374, 375 are actuated, thereby screwing the implant 370 to the surrounding bone substance. In this process, the threaded section 382 along with the remaining parts of the through-opening 372 guides the screw bolts so that they can penetrate the surrounding bone substance in a predefined orientation.

The through-openings 372, 373 have at their dorsally located openings at the surface of the implant 370 a larger diameter so that the screw bolts 374, 375, when in the screwed-in state, can be fully received with their bolt head 384 within the body of the implant 370. This region 386 of expanded diameter of the through-openings 372, 373 is adjoined by the previously mentioned section having an internal thread 382 therein.

The screw bolts 374, 375 are preferably configured such that they have, in the area thereof that is adjacent to the bolt head 384, an unthreaded shank portion 388 which is long enough to extend through the internal thread 382 of the through-opening 372 so that, when the screw bolts 374, 375 are fully screwed in, the thread of the screw bolts comes out of engagement with the internal thread 382 and as a result, by tightening the screw bolts 374, 375, the contact faces of the implant body 380 can be brought in close contact with the incision faces of the bone substance.

The length of the screw bolts 374, 375 is dimensioned such that even after they have been screwed fully into the implant body 380, they do not protrude from the implant body far enough to penetrate the spinal canal. In the fully screwed-in state, the point of the screw bolts 374, 375 is therefore preferably positioned so as to remain rearward of the ventral front edge 390 of the implant 370.

Figure 20A:
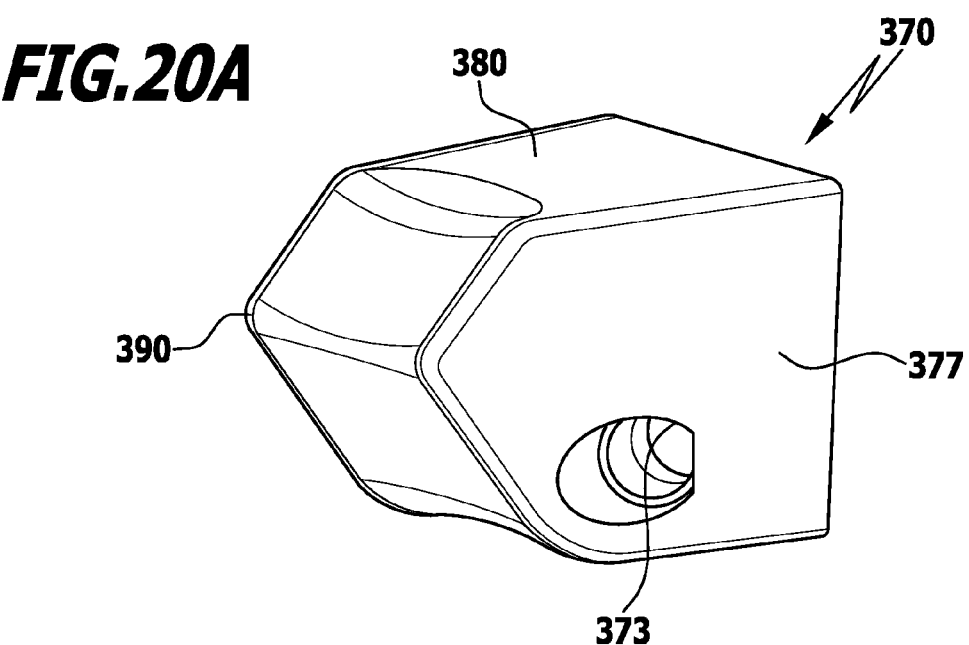
Figure 20B:
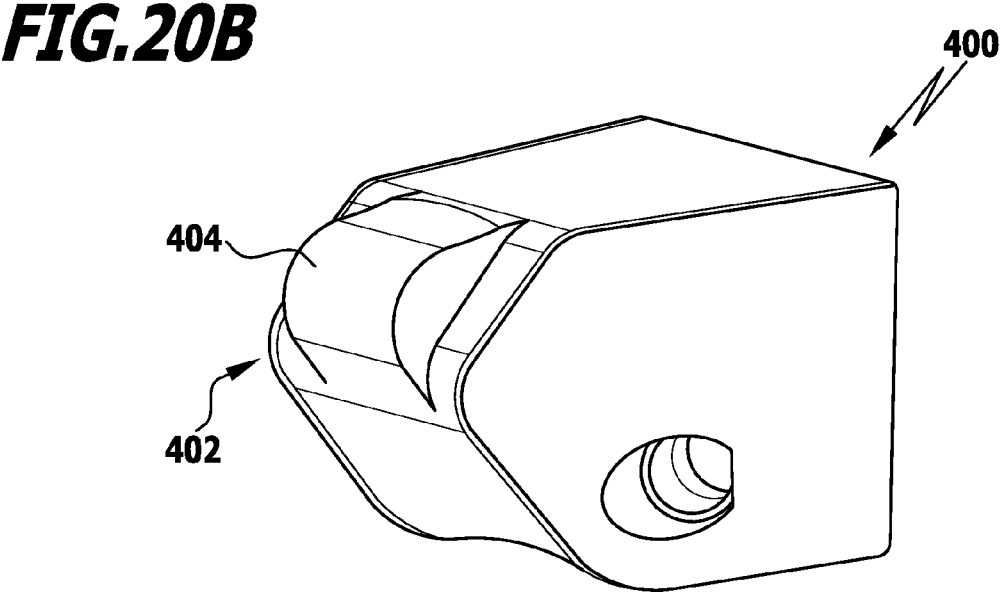

For comparison with the variants depicted in FIGS. 20B to 20D, FIG. 20A shows once again the implant 370 from FIG. 19, this time a perspective view of the ventral, or distal, end region 390 (front edge) of the implant, which is provided with an indentation so that additional volume is created adjacent to the spinal canal.

In the alternative of FIG. 20B, the implant 400 has a structure that is substantially similar to that of the implant 370, except that the ventral end region 402 has integrally formed thereon a nose 404 which, when the implant is inserted into the incision gap of the vertebral arch, can engage between the arms of distraction forceps so that the implant 400 can be introduced into the incision gap of the vertebral arch in a guided, in particular centred, manner.

FIG. 20C shows an implant 410 wherein the ventral end region 412 is of planar configuration and thus forms a stop face 414 which in the final inserted state of the implant 410 in the incision gap enables contact over a large area thereof with the distraction forceps or the stop elements thereof.

A further variant of an implant constructed in accordance with the invention is shown in FIG. 20D. The implant 420 shown therein has a ventral end region 422 which, similar to the embodiment of FIG. 20B, has a nose 424 which projects therefrom and likewise ensures that the implant 420 is guided during insertion by the implant 420 being able to engage therewith between the arms of a distraction instrument.

In order to improve manipulation of the implants constructed in accordance with the invention, it is preferred for them to be fixed to a holding or inserting instrument, and preferred implants have corresponding features for connecting to the holding or inserting instrument, such as a bore in the dorsally located end face, as illustrated in FIGS. 19A and 19B with the example of bore 392. A holding or inserting instrument can be fixed in said bore 392 in a direction parallel to the longitudinal direction of the implant.

Figure 21B:
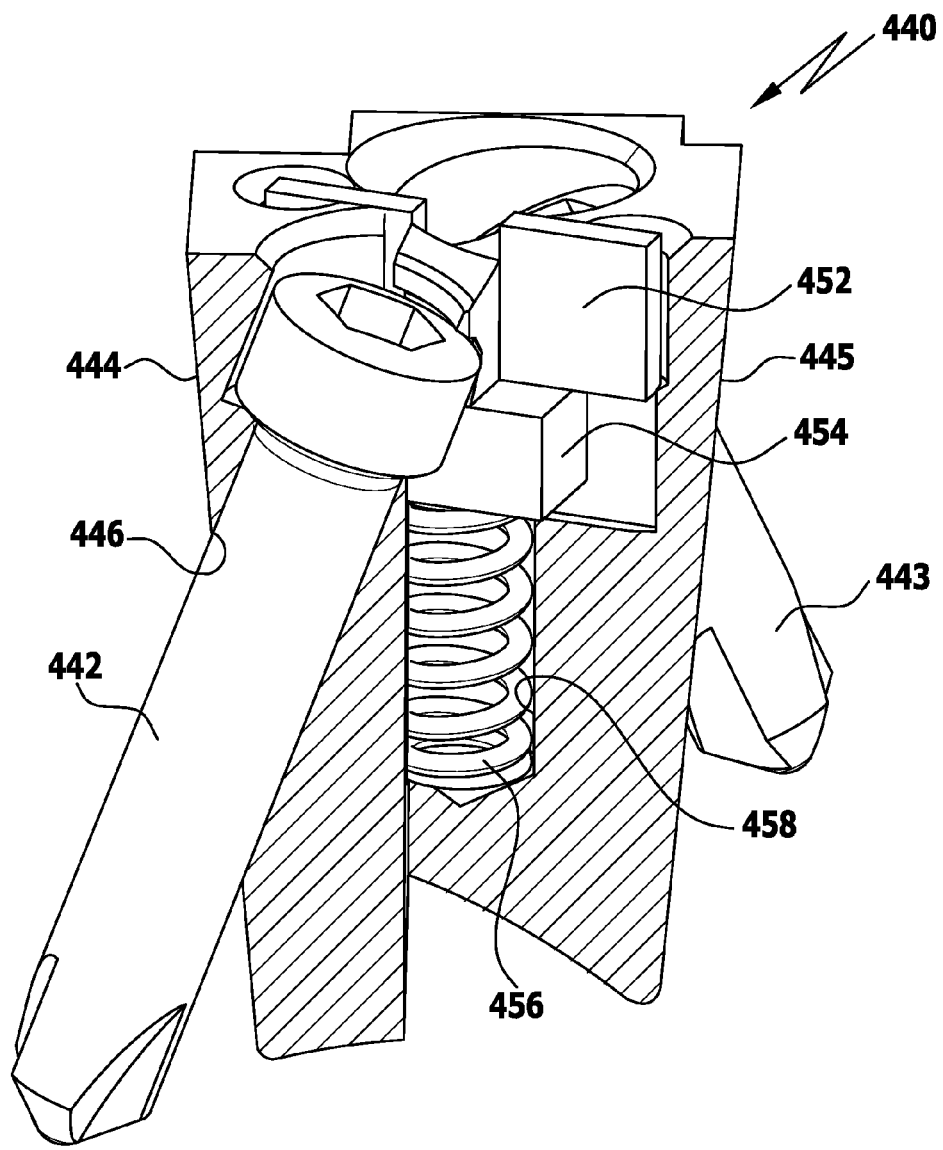
Figure 21C:
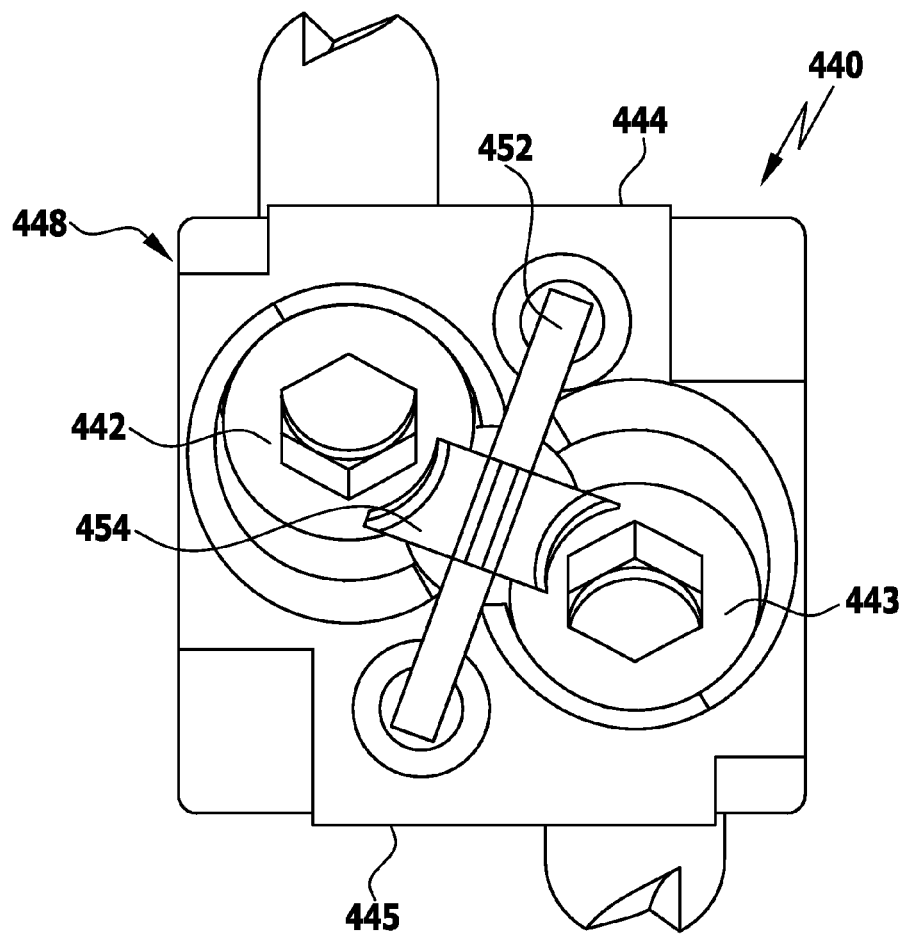

A further aspect of the implants constructed in accordance with the invention will be discussed in greater detail in conjunction with FIGS. 21A to 21C.

FIG. 21 shows different views of an implant 440 which, similar to the implant 370 of FIG. 19, is fixated in the surrounding bone substance via screw bolts 442, 443. For receiving and guiding the screw bolts 442, 443, the implant 440 has through-openings 446, 447 which extend at an acute angle with respect to contact faces 444, 445 and, starting from a dorsal end region 448 of the implant 440, exit from the contact faces 444, 445 and at that point allow the screw bolts 442, 443 to penetrate the surrounding bone substance.

In order to prevent the screw bolts from coming loose over time, a locking device 450 is provided which comprises a slider 452, a locking element 454 and a helical spring 456. In order to receive the locking device 450, the implant 440 has provided therein a central blind bore 458 which starts from the dorsal end and in which the spring 456 is received when in the assembled state. Provided above the blind bore 458 is a receptacle for the locking element 454 and the slider 452, guidingly holding these. For inserting the implant 440 into an incision gap of a vertebral arch, a holding or inserting instrument is preferably used which is fixed to the dorsal end region 448 of the implant 440.

Preferably, fixing the inserting or holding instrument to the implant 440 causes the slider 452 to be urged downwards, i.e., against the ventral end of the implant 440, simultaneously causing the locking element 454 to be pushed out of its active locking position.

Once the implant is inserted in the incision gap of the vertebral arch and with the holding element still fixed to the implant 440, the screw bolt 442 and the screw bolt 443 are screwed into the surrounding bone material. With the implant 440 thus fixated in the incision gap of the vertebral arch, the holding and inserting instrument can be separated from the implant 440, whereupon the locking device 450 is activated, causing the locking element 454 together with the slider 452 to be displaced in a direction towards the dorsal end region 448 by way of the spring 456. In this process, the locking element 454 glides into a dorsal side end position in which it blocks the screw bolts 442, 443 from loosening, as shown more particularly in FIGS. 21B and 21C, which are a perspective and a top view respectively.

Figure 22A:
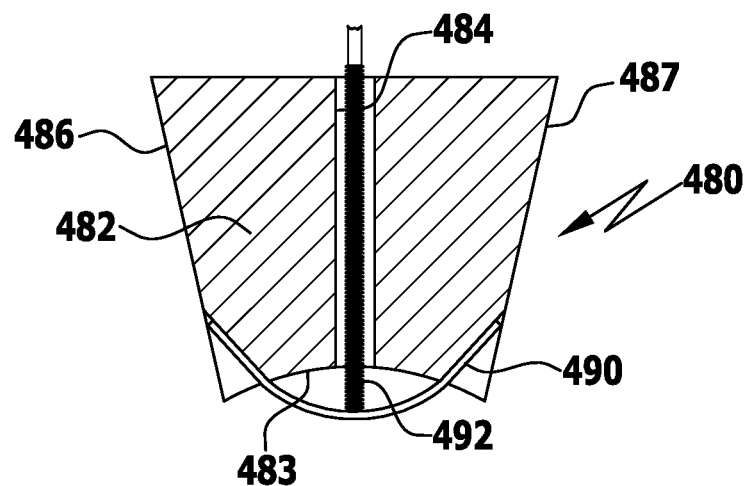
FIGS. 22A to 22C are sectional views of a variant of the third embodiment of the first basic form of the implant constructed in accordance with the invention, in different states during implantation.

A further variant of an implant constructed in accordance with the invention is shown in views A to C of FIG. 22; here, a further variant for fixating the implant 480 in its position in the incision gap of a vertebral arch is to be explained.

The implant body 482 of the implant 480 has a longitudinal bore 484 which extends essentially from the dorsal to the ventral end region of the implant 480 and is arranged generally centrally between the contact surfaces 486, 487 arranged in the shape of a wedge.

At its ventral end, the implant body 482 has, in addition to an indentation 483 for increasing the volume on the spinal canal side as has already been described in conjunction with the previous embodiments, recesses 488, 489 that are located adjacent to its contact faces 486, 487.

The implant 480 uses a sheet-like spring element 490 as a holding element, which may be of strip-like configuration for example. Centrally fixed to the holding element 490 is a pin 492 which extends dorsally through the implant body 482 or the longitudinal bore 484 thereof.

In the state ready to be installed, the implant 480 has the holding element 490 in the configuration shown in view A of FIG. 22 in which the free ends of the holding element 490 are bent back into and resiliently engage the recesses 488, 489.

Figure 22B:
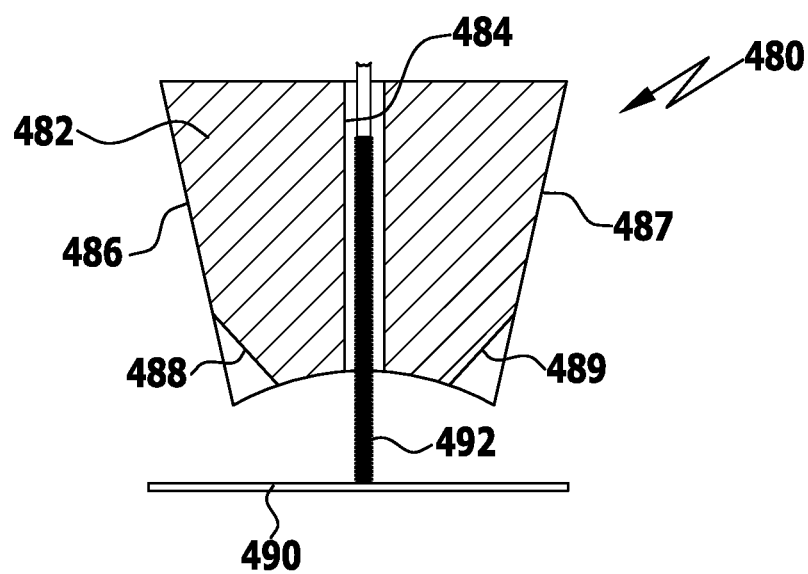

In the inserted state of the implant 480, the fixing of the holding element 490 in the recesses 488, 489 is then released via the pin 492 so that the holding element 490 can then unfold and assume a substantially flat configuration as illustrated in the FIG. 22B view.

Figure 17B:
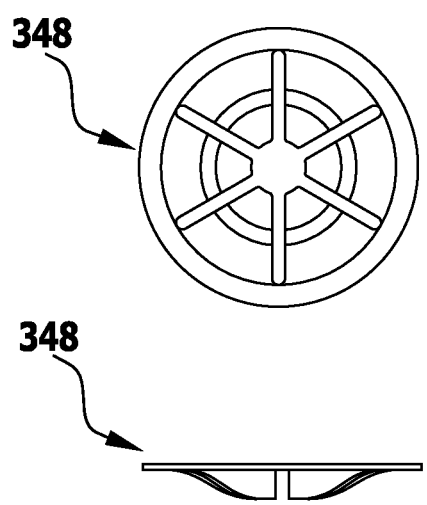

To fixate the implant 480 in the incision gap of a vertebral arch, the holding element 492 is then pulled in a dorsal direction and is then, in this position, fixated on the upper side of the implant 480 using a holding element 494 as it is exemplified more particularly in FIG. 17B. At this point, the spring element 490 contacts the inside of the vertebra's lamina on either side of the incision gap and contacts the underside, the ventral side, of the implant 480, thus providing for fixation of the implant in the incision gap of the treated vertebra, as illustrated in view C of FIG. 22.

FIG. 23 shows two variants of the implant 480. Shown in FIGS. 23A and 23B is an implant 500 which has a central bore 502 extending from the dorsal end region to the ventral end region of the implant 500.

This through-opening 502 receives for displacement therein a pin 504 which centrally holds at its ventral end a holding element 506 in the form of a spring sheet metal strip. With the implant 500 in the state ready to be implanted, the spring metal sheet 506 is held against a ventral indented face 510 of the implant 500 with its two free ends rolled in. Once the implant 500 is inserted in the incision gap of a vertebral arch, the pin 504 is urged downwards, similar to what has been described in conjunction with FIG. 22, so that the spring metal sheet 506 can unfold. Thereupon, the pin 504 is pulled in a dorsal direction so that the spring metal sheet 506 in the unfolded state as shown in FIG. 23B is in surface contact with and projects beyond the indented ventral side 510 of the implant 500 so that surface contact with the adjacent vertebral arch (not shown) results, as has already been shown more specifically in conjunction with the implant 480 in FIG. 22C.

Figure 23A:
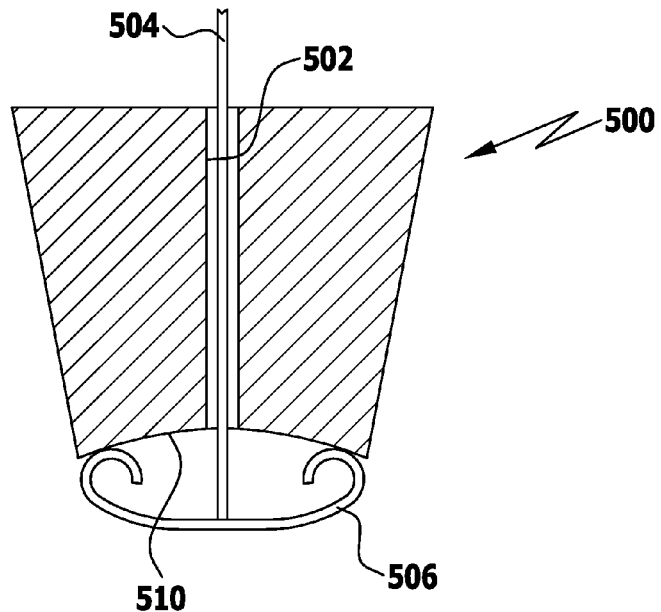
FIGS. 23A to 23D is a schematic side view of two further variants of the third embodiment of the first basic form of the implant constructed in accordance with the invention.
Figure 23B:
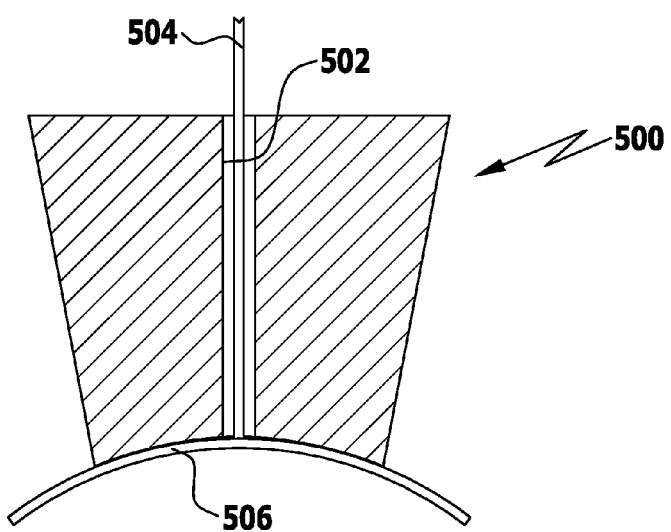
Figure 23C:
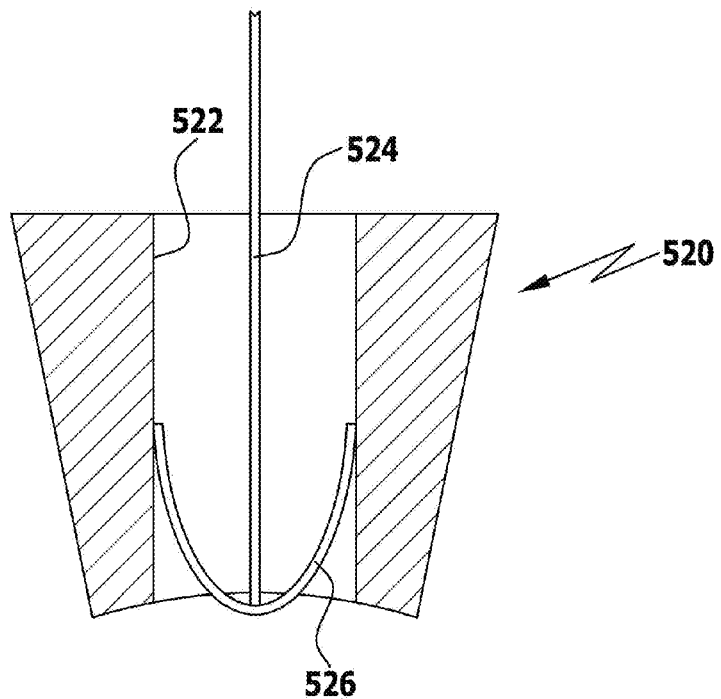
Figure 23D:
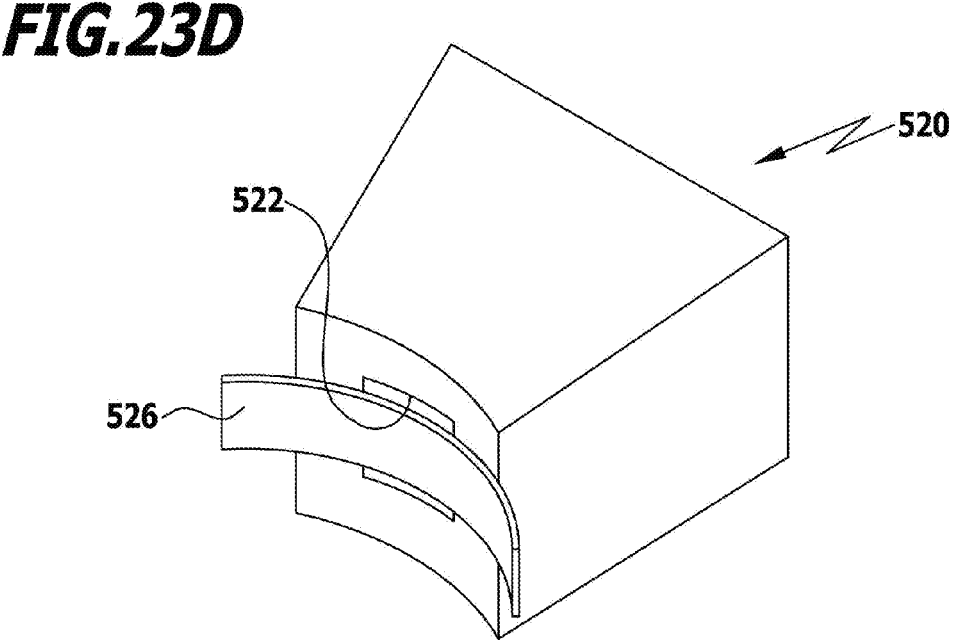

Alternatively, an implant 520 as shown in FIG. 23C can have a relatively large through-bore 522 which receives not only a holding pin 524 but also a spring metal sheet 526 which is bent together to form a U-shape and is centrally connected to one end of the holding pin 524.

Again, once the implant 520 is inserted in the incision gap of a vertebral arch, the pin 524 is urged downwards, i.e., in a ventral direction, so that the spring metal sheet 526 can then unfold. Thereupon, again, the pin 524 is pulled in a dorsal direction so that the spring metal sheet 526 comes into contact with the ventral side of the implant 520. The areas of the spring metal sheet 526 projecting from either side of the implant 520 then contact parts of the bone substance of the vertebral arch.

Figure 22C:
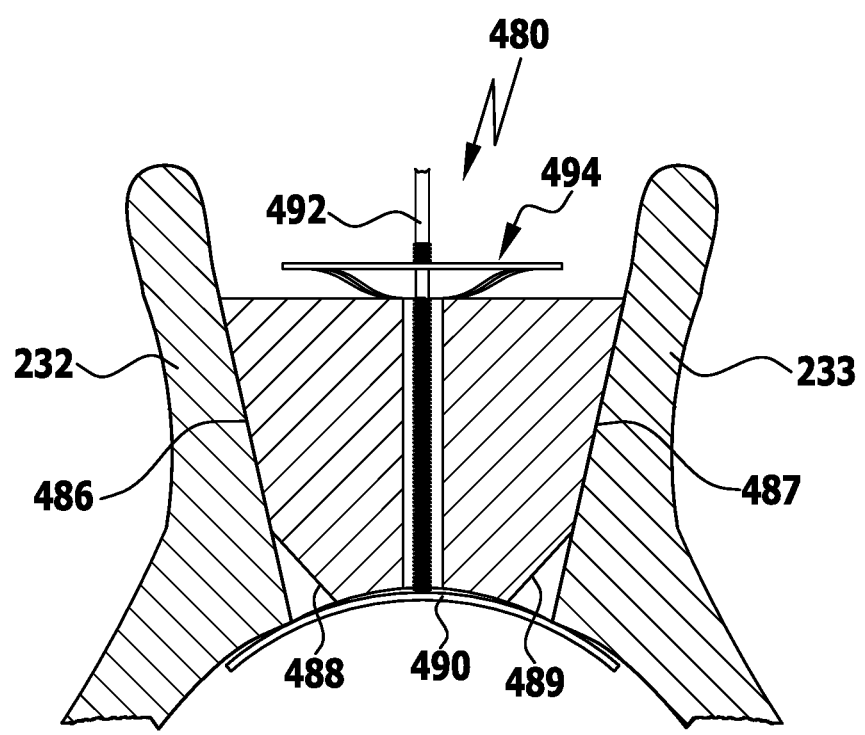

The pin 524 in its retracted position in which the spring metal sheet 526 contacts the ventral side of the implant 520 can be held in place by way of a fixation element similar to the fixation element 494 of FIG. 22C.

Two further alternative embodiments of an implant constructed in accordance with the invention are shown in FIG. 24. In the implant 530 of FIG. 24A, the implant body 532 has a continuous bore 534 extending from the dorsal to the ventral side thereof. Similar to what is shown for the embodiment of FIG. 22, a pin 536 extending through the bore 534 from ventral to dorsal holds at its ventrally located end a spring metal sheet 538. The spring metal sheet 538 is bent together and, in the bent-together state, fixed in recesses 540, 541 on the ventral side of the implant 530. As with the embodiment of FIG. 22, the spring metal sheet 538 unfolds as the pin 536 is urged in a ventral direction and can then be brought into surface contact with the ventral side of the implant 530 and the adjacent bone substance portions of the vertebral arch by retracting the pin 536.

Figure 24A:
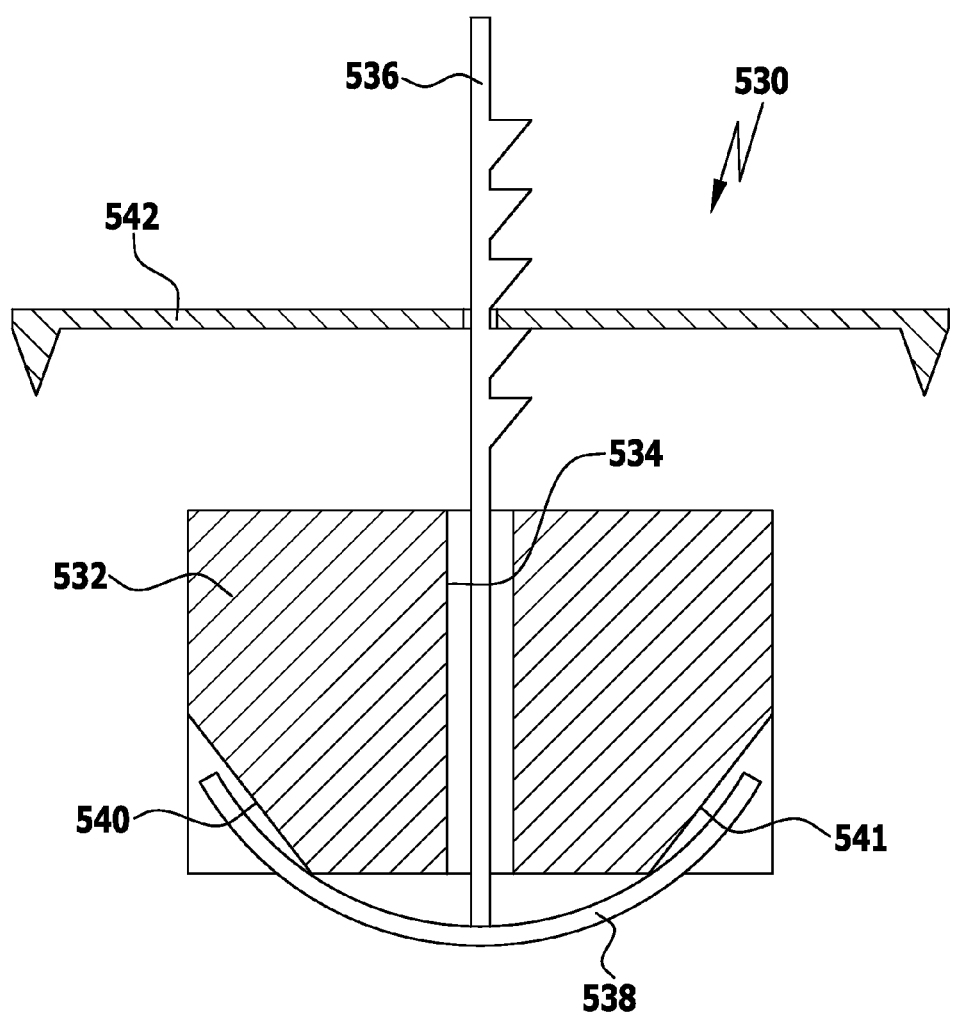
FIGS. 24A to 24D show two variants of a fourth basic form of the implant constructed in accordance with the invention.
Figure 24B:
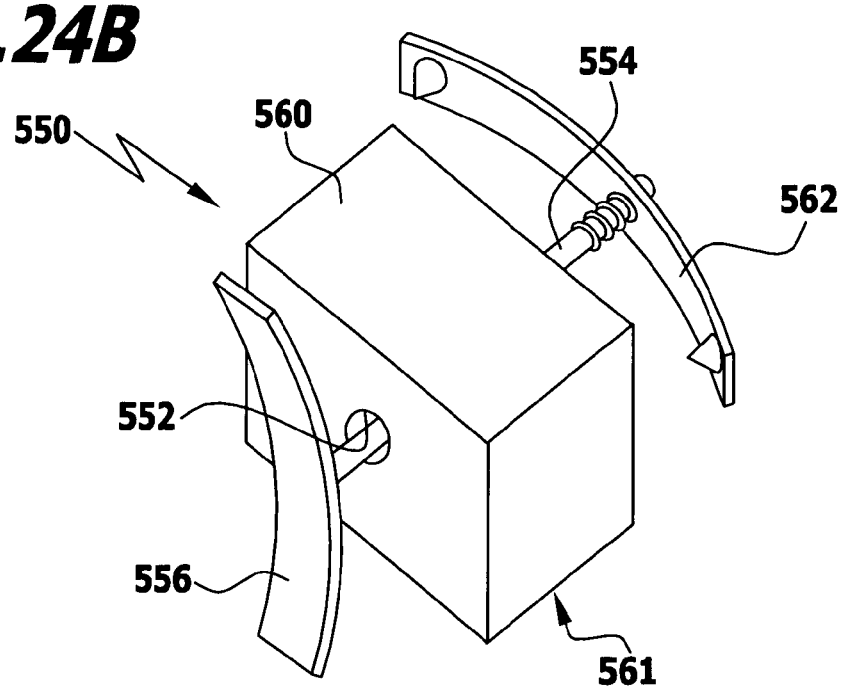
Figure 24C:
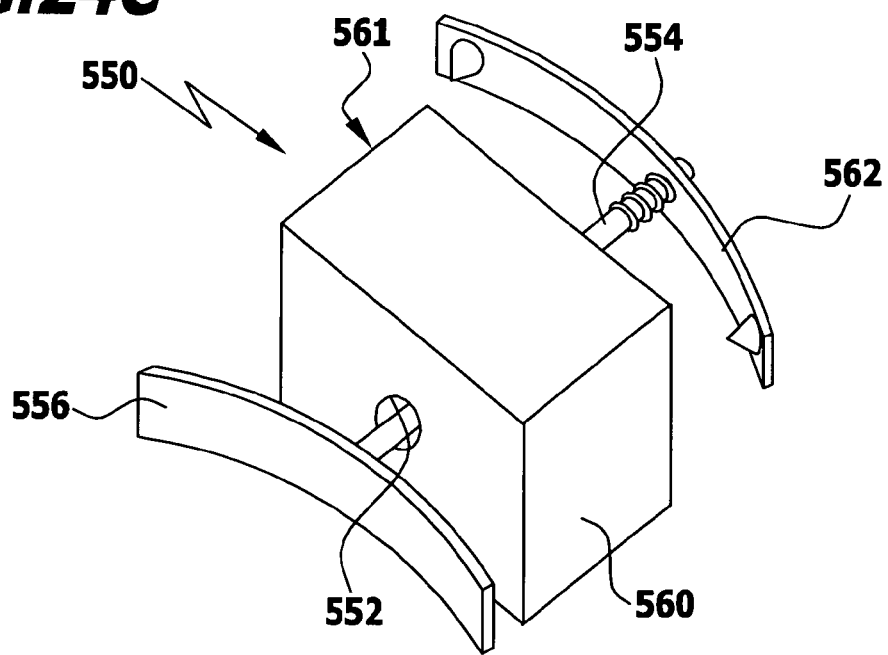
Figure 24D:
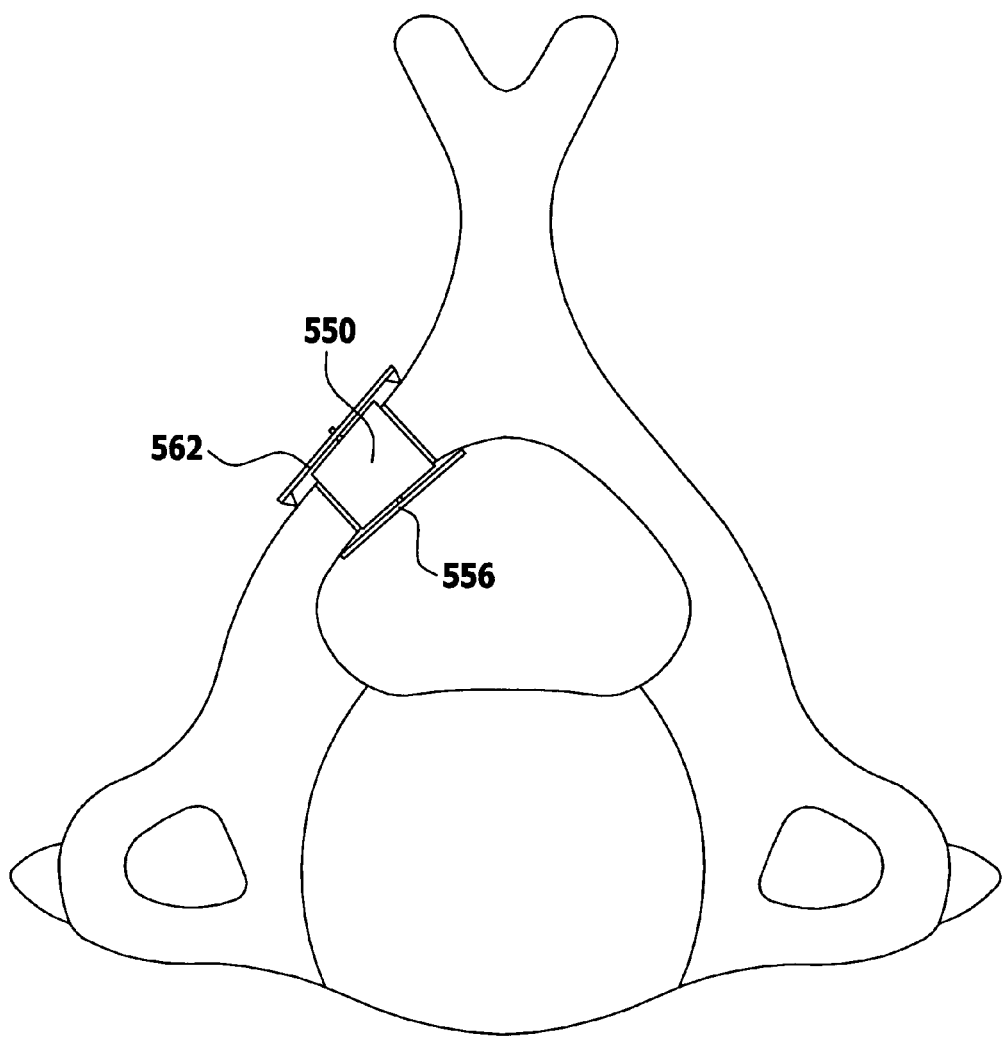

Unlike the FIG. 22 embodiment, the holding pin 536 is now fixated in its retracted position by a second spring metal sheet 542 engaging over the implant body 530, said second spring metal sheet 542 engaging over the implant body on both sides thereof and contacting the bone substance on the distal side of the vertebral arch (comparable with the situation depicted in FIG. 24D).

A further variant is illustrated in FIGS. 24B and 24C, in which an implant 550 again has a through-opening 552 which extends from the ventral to the dorsal side and has a holding pin 554 guided therein. At its ventral end, the pin 554 holds a spring sheet metal strip 556 which is oriented in a sagittal direction so long as the implant 550 is not yet inserted in the incision gap of a vertebral arch. Once the implant has been inserted in the incision gap of a vertebral arch, the spring metal sheet 556 is turned through about 90° so that it then protrudes beyond the contact faces 560, 561 of the implant 550 and can subsequently, after the pin 554 has been retracted in a dorsal direction, be brought in contact with the bone substance of the vertebral arch.

On the dorsal side, the holding pin 554 carries a securement element 562 which likewise engages over the contact faces 560, 561 of the implant 550 so that an installed situation of the implant in the vertebral arch results as it is shown in FIG. 24D.

Figure 25:
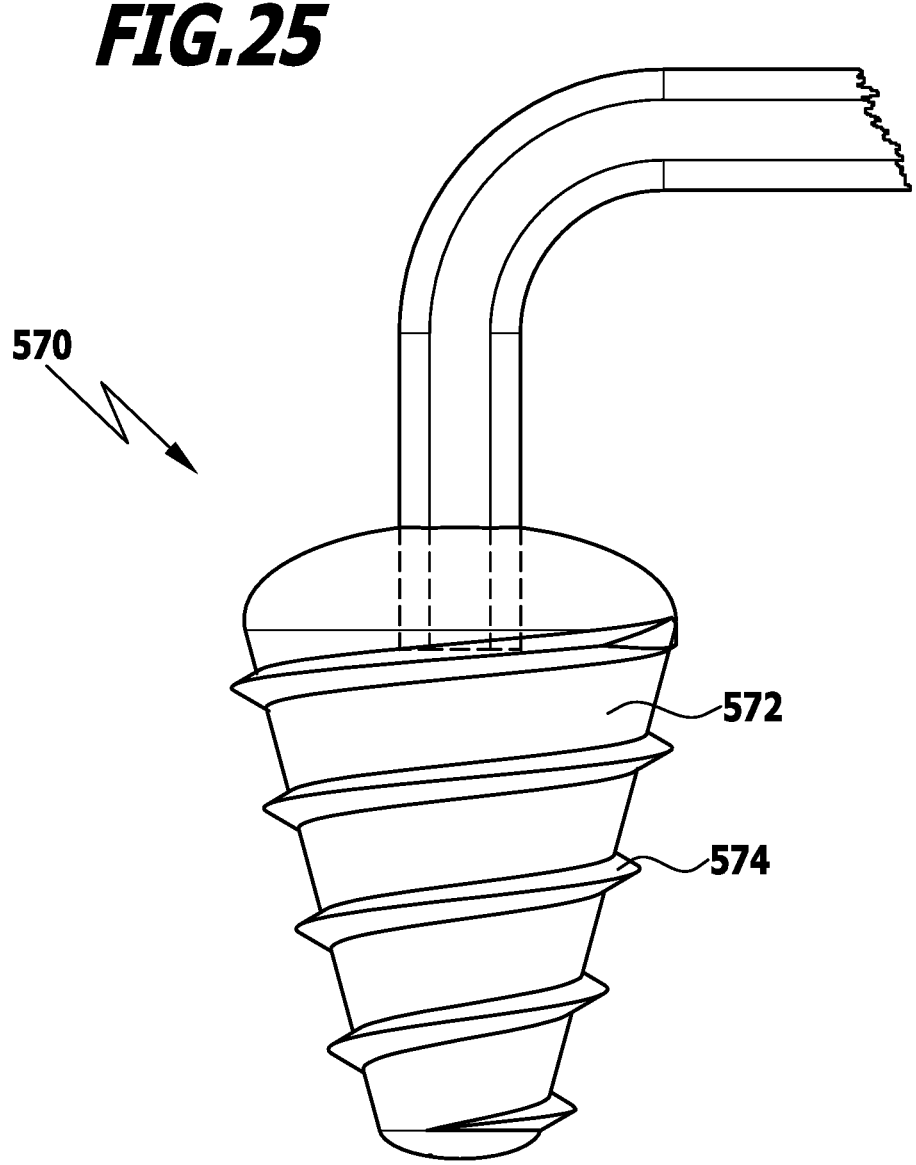
FIG. 25 depicts a fifth basic form of the implant constructed in accordance with the invention.

FIG. 25 shows a further embodiment of an implant 570 constructed in accordance with the invention, comprising a conical implant body 572 which has a screw thread 574 on its outer surface. Unlike the previously described implants, the implant 570 does not necessitate a widened incision gap for its insertion. It is advantageous for the incision gap created by cutting through the lamina to comprise opposed recesses in the incision faces dorsally, the ventral end region of the implant 570 being first received and centred in said recesses.

When the implant 570 is subsequently screwed into the incision gap, the thread 574 cuts a mating thread into the bone substance. Due to the conical shape of the implant body 572, the incision gap is successively widened during the screwing-in so that the lamina sections are gradually elastically/plastically deformed.

Figure 26:
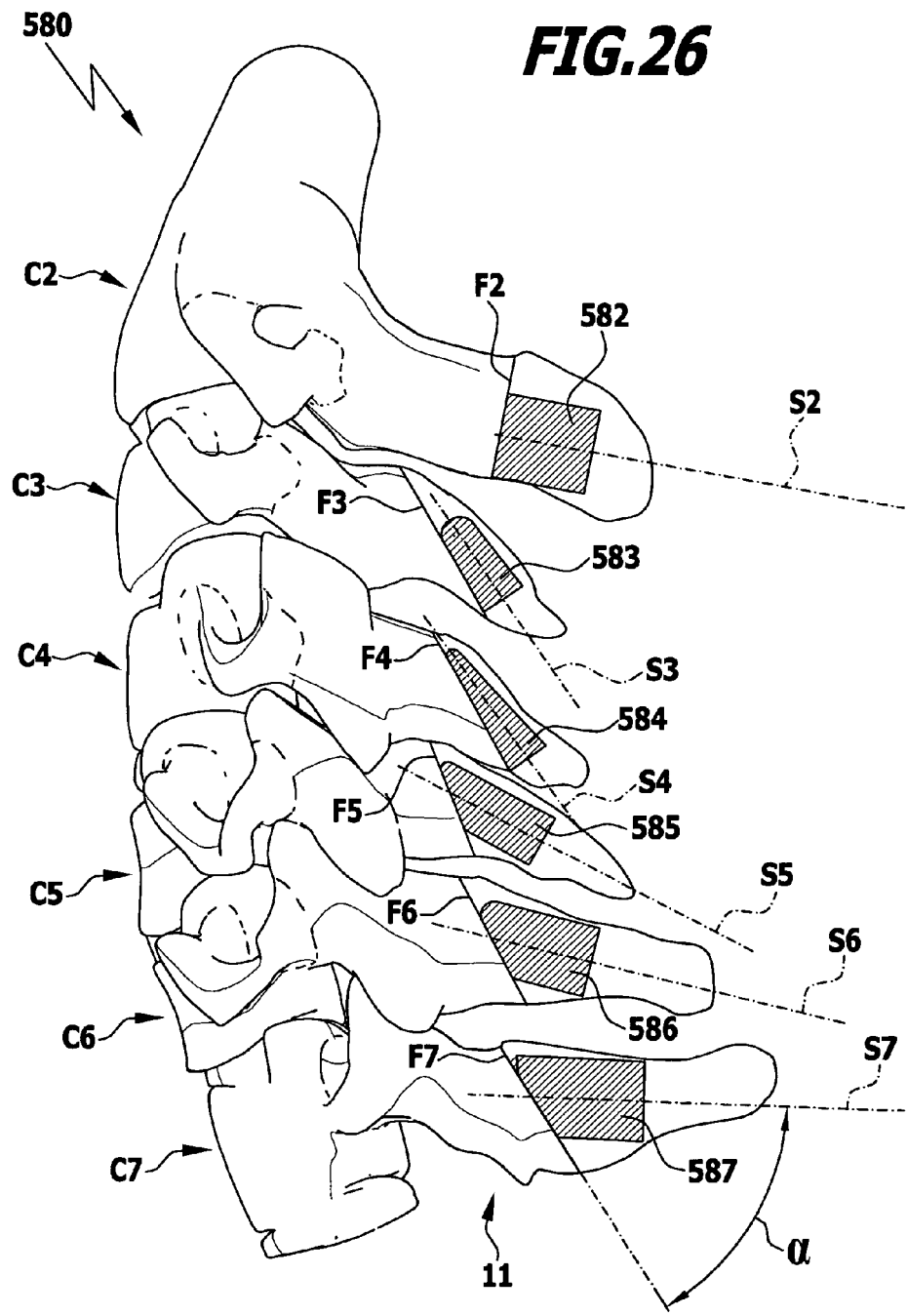
FIG. 26 illustrates a section of a cervical spine shown as having inserted therein implants constructed in accordance with the invention and based on the first basic form.

FIG. 26 is a side view, partially broken open (along the incision gaps 20), of a cervical spine section 580 in which the cervical vertebrae C2 to C7 are each held in a widened state of the vertebral canal by an implant body 582, 583, 584, 585, 586, 587. Depending on the shape and size of the spinous process of the respective cervical vertebrae C2 to C7, implant bodies 582 to 587 of different size and different configuration are used, and these are inserted with their longitudinal axis in each case in a substantially parallel orientation to the longitudinal axis S2, S3, S4, S5, S6, S7 of the spinous process.

The back wall of the vertebral canal (spinal canal 11) is designated by reference characters F2 to F7 in the cervical vertebrae C2 to C7. It represents in each case the dorsal boundary of the spinal canal and the anterior boundary of the lamina.

For optimum adaptation of the implant bodies to the respective vertebra, the C2 vertebra for example requires a large, diamond to rectangular cross-section, the C3 and C4 vertebrae require a long and rather flat, wedge-shaped cross-section, whereas the C6 and C7 vertebrae require rather short and thicker wedge shapes of the implant bodies 586, 587.

Figure 27:
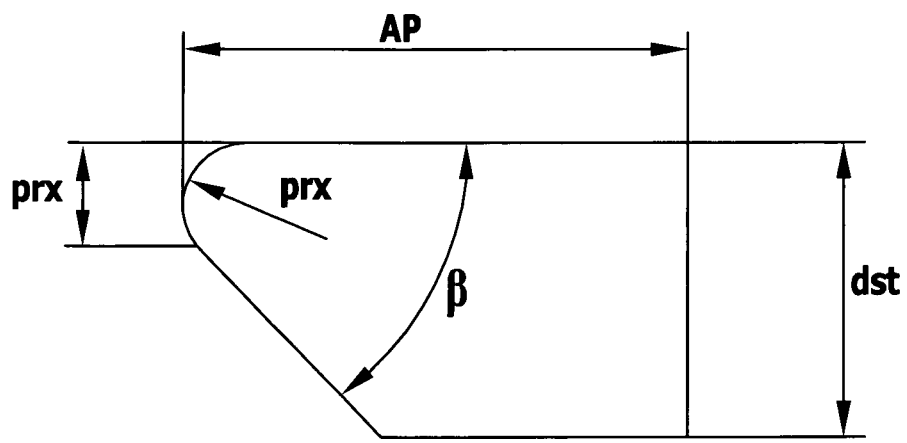
FIG. 27 is a schematic representation of an implant body constructed in accordance with the invention, for parameter definition.

The individual parameters which characterize these implant bodies are shown in FIG. 27 and exemplified numerically in Table 2.

TABLE 2

|    | Width dst | Length AP | Inclination $\beta$ [°] | Residual width prx | Radius prx | $\alpha$ [°] |
|----|-----------|-----------|-------------------------|--------------------|-----------|--------------|
| C1 | —         | —         | —                       | —                  | —         | —            |
| C2 | 8.381     | 10.324    | —                       | —                  | —         | 72.61        |
| C3 | 4.611     | 9.686     | 16.51                   | 1.508              | 1.508     | 33.4         |
| C4 | 4.031     | 12.963    | 12.96                   | 1.682              | 0.841     | 36.41        |
| C5 | 5.249     | 12.963    | 39.83                   | 1.015              | 0.58      | 55.24        |
| C6 | 7.018     | 11.629    | 47.65                   | 2.407              | 1.479     | 69.84        |
| C7 | 7.917     | 12.325    | 56.48                   | 2.088              | —         | 81.19        |

The angle $\alpha$ is defined as the angle formed between the back walls F2 to F7 (generally designated Fi) and the corresponding longitudinal axes S2 to S7 (generally designated Si).

In the widening of the incision gap 20 in accordance with the invention, it is preferred for a distraction tool to be inserted by the surgeon from a cranial position into the incision gap. To this end, distraction tools are preferably used which have at their distal end outwardly protruding flanges or ribs which are guided along the back wall Fi. The back wall Fi serves as a depth stop.

When the implant is inserted with an insertion tool, the distraction tool positioned in the incision gap and/or the back wall Fi of the spinal canal may serve to orient the implant along the longitudinal axis Si of the respective spinous process, for example when the implant inserted in the incision gap is turned about the stop formed by the distraction tool.

Figure 28:
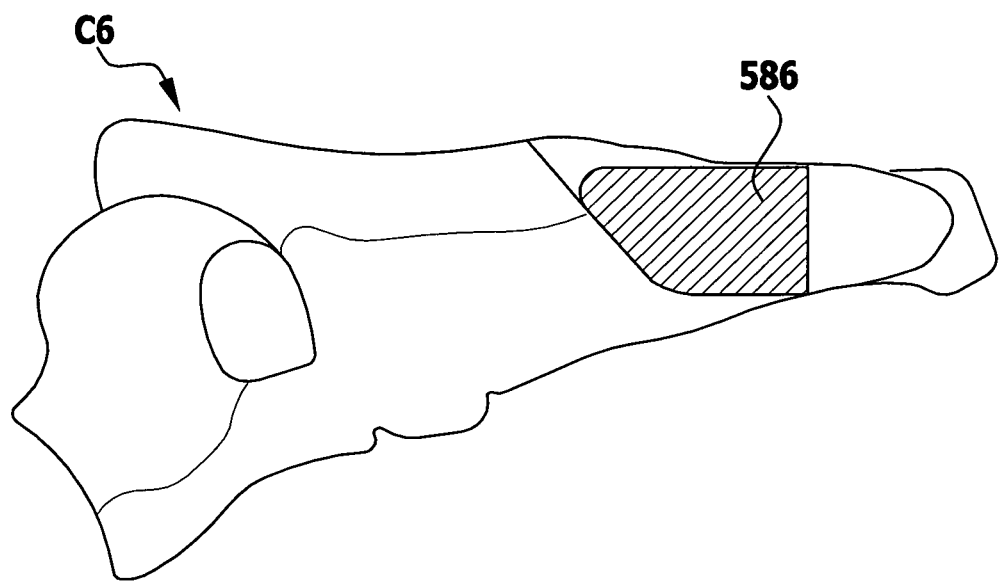
FIG. 28 is a detail view of an implanted implant constructed in accordance with the invention and illustrated in FIG. 26, with the C6 vertebra shown partly broken open.

Using the C6 implant 586 as an example, FIG. 28 illustrates the installed situation thereof in the incision gap of the spinous process of the C6 vertebra, with the spinal canal shown broken open.

Figure 29A:
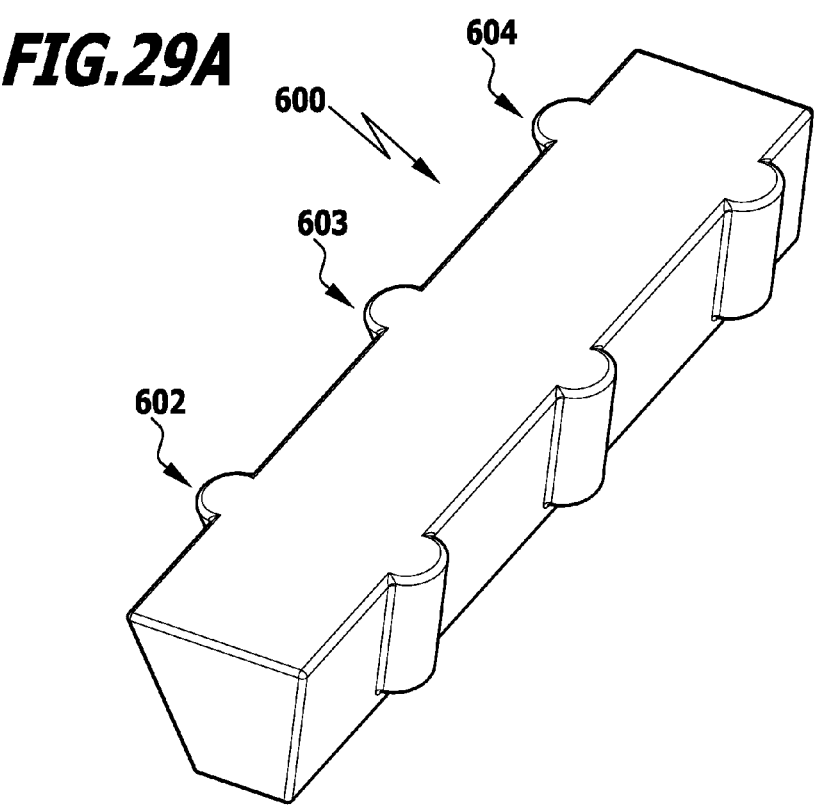
FIGS. 29A and 29B are a perspective view and a top view of a first embodiment of a multiple implant constructed in accordance with the invention and based on the first basic form, in the implanted state.
Figure 29B:
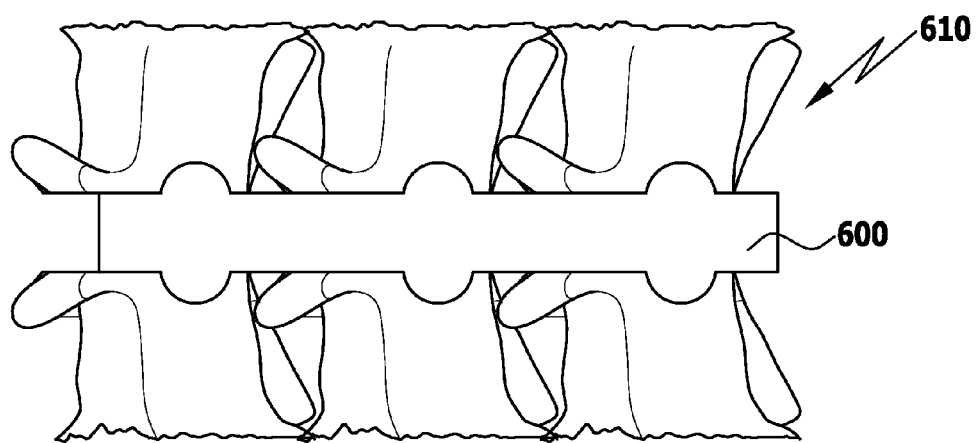

FIG. 29 shows a first embodiment of a multiple implant 600 which is suitable for insertion as a single implant into incision gaps created in successive vertebrae. The configuration of the multiple implant 600 corresponds substantially to that of the implant 80 of FIG. 6 in terms of the implant area 602, 603, 604 or the incision gap provided per vertebra. The top view schematically exemplifies the implanted state in a section of the cervical spine 610. Because the implant areas are essentially rigidly connected to one another, they lead to stabilization and a certain immobilization of the treated section of the spine.

FIG. 30 shows a second embodiment of a multiple implant 620 in which the individual implant sections 622, 623, 624 are not rigidly but movably connected to one another. Such a connection may in particular be of articulated configuration and more preferably, as shown in FIG. 30, of elastic configuration in a sagittal direction, for example by use of helical springs 626. Here too, stabilization of the treated spine section 610 occurs, but without the immobilization which in some cases is undesired.

Figure 31:
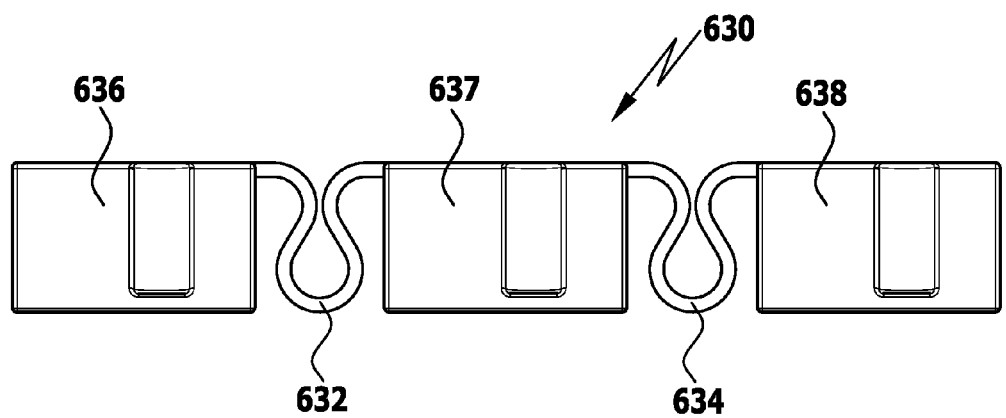
FIG. 31 is a side view of a third embodiment of an implant constructed in accordance with the invention and based on the first basic form.

A variant of the multiple implant 620 of FIG. 30 is shown in FIG. 31. The multiple implant 630 shown therein comprises in lieu of the helical springs 626 leaf springs 632, 634 in order to couple the implant sections 636, 637, 638 to one another movably and resiliently.

Figure 32:
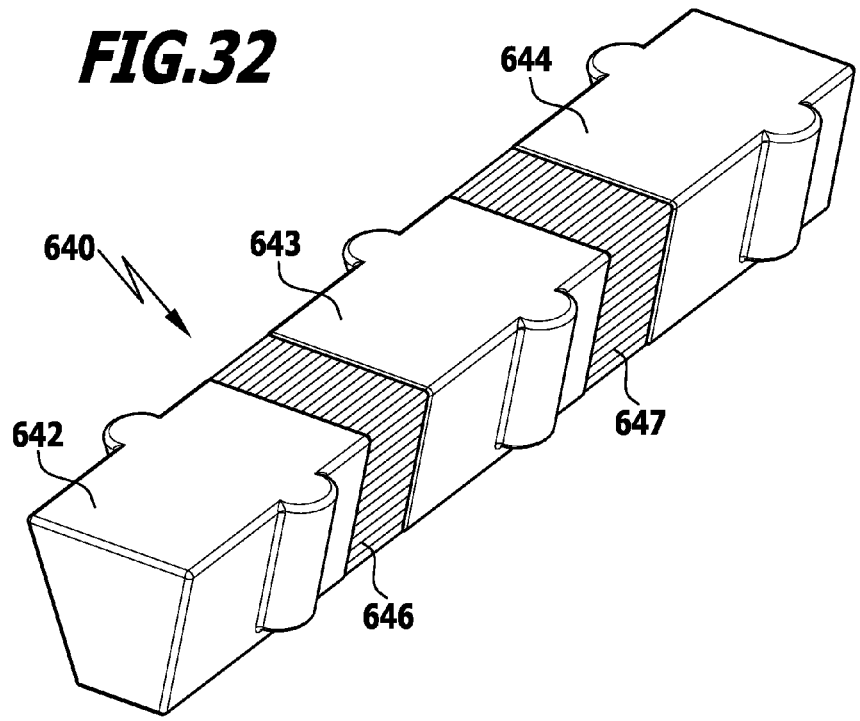
FIG. 32 is a perspective view of a fourth embodiment of a multiple implant constructed in accordance with the invention and based on the first basic form.

A further variant of the multiple implant 620 of FIG. 30 is shown in FIG. 32. In this multiple implant 640, the elastic connection between the individual implant sections 642, 643, 644 is accomplished by way of elastomer bridges 646, 647. The elastomer bridges 646, 647 can be adjusted in their elasticity such that the desired mobility is maintained between the individual vertebrae, while undesirably large movements that might adversely affect the success of the treatment are hindered or even prevented.

What is claimed is:

1. Implant for use in a laminoplasty or laminectomy method in which a vertebral arch of a vertebra is cut through, forming an incision gap, or in which the vertebral arch is partially removed and the implant is inserted in the incision gap, wherein the incision gap is bounded by incision faces opposed to each other, wherein the implant comprises:
   an implant body having two contact faces which in an inserted state in the incision gap are configured to contact incision faces of the vertebral arch,
   a fixation device comprising one or more fastening elements in a form of at least one of (i) one or more screws, (ii) one or more bolts, and (iii) one or more dowels, which are transitionable from an inoperative position to an operative position by one or more actuating devices,
   wherein tips of the one or more fastening elements in the inoperative position are arranged within a contour of the implant body and in the operative position are configured to emerge from openings in the contact faces into surrounding bone substance.

2. Implant in accordance with claim 1, wherein the contact faces of the implant body have guide elements arranged thereat.

3. Implant in accordance with claim 2, wherein:
   the implant body is of a wedge-shaped configuration; and
   the guide elements are essentially configured as projections or recesses which are oriented substantially parallel to a longitudinal axis of the wedge-shaped implant body.

4. Implant in accordance with claim 3, wherein:
   the contact faces are inclined relative to each other in a shape of a wedge,
   a distance between the contact faces is larger at a dorsal end region of the implant body than at a ventral end region thereof.

5. Implant in accordance with claim 3, wherein the recesses of the guide elements are configured as grooves.

6. Implant in accordance with claim 5, wherein the grooves are configured to extend substantially parallel to a longitudinal direction of a spinous process.

7. Implant in accordance with claim 5, wherein the recesses are of substantially semi-cylindrical configuration.

8. Implant in accordance with claim 1, wherein the implant body has a guide element at a ventral end thereof.

9. Implant in accordance with claim 1, wherein the implant body has a stop element which is configured to come into contact with the surrounding bone substance and limits an insertion depth of the implant in the incision gap to a predetermined value.

10. Implant in accordance with claim 1, wherein the implant body has longitudinal bores which are oriented substantially parallel to a longitudinal axis of the implant body and are freely accessible at least on a dorsal side of the implant body.

11. Implant in accordance with claim 1, wherein the implant body has one or more transverse bores which are oriented transversely to a longitudinal axis of the implant body.

12. Implant in accordance with claim 11, wherein the one or more transverse bores comprise through-bores.

13. Implant in accordance with claim 1, wherein the implant body has bores which, starting from a dorsal end region of the implant body, are oriented at an acute angle with respect to the contact faces of the implant body.

14. Implant in accordance with claim 13, wherein the bores extend through the contact faces.

15. Implant in accordance with claim 1, wherein:
   the one or more fastening elements comprise the one or more dowels; and
   the one or more dowels are plastifiable by one of heat, ultrasound, UV light or HF radiation.

16. Implant in accordance with claim 1, wherein:
   the one or more fastening elements comprise the one or more dowels; and
   the one or more dowels are heat-bondable.

17. Implant in accordance with claim 1, wherein a ventral end region of the implant body is of a convex configuration.

18. Implant in accordance with claim 1, further comprising a grip element at a dorsal end region of the implant body.

19. Implant in accordance with claim 1, wherein the implant body has at a ventral end region a distance between the contact faces that is about 5 mm to about 15 mm.

20. Implant in accordance with claim 1, wherein the contact faces are configured such that they are supported over essentially an entire area thereof on the incision faces of the incision gap.

21. Implant in accordance with claim 1, wherein the contact faces are substantially planar.

22. Implant for use in a laminoplasty or laminectomy method in which a vertebral arch of a vertebra is cut through, forming an incision gap, or in which the vertebral arch is partially removed and the implant is inserted in the incision gap, wherein the incision gap is bounded by incision faces opposed to each other, wherein the implant comprises:
   an implant body having two contact faces which in an inserted state in the incision gap are configured to contact incision faces of the vertebral arch, and
   one or more fastening elements in a form of one or more dowels which are plastifiable by one of heat, ultrasound, UV light, or HF radiation.

23. Implant for use in a laminoplasty or laminectomy method in which a vertebral arch of a vertebra is cut through, forming an incision gap, or in which the vertebral arch is partially removed and the implant is inserted in the incision gap, wherein the incision gap is bounded by incision faces opposed to each other, wherein the implant comprises:
   an implant body having two contact faces which in an inserted state in the incision gap are configured to contact incision faces of the vertebral arch, and
   one or more fastening elements in a form of one or more dowels which are heat-bondable.

* * * * *